(12) United States Patent
Heuer et al.

(10) Patent No.: US 10,253,294 B2
(45) Date of Patent: Apr. 9, 2019

(54) GALACTOSE OXIDASE TREATMENT OF DENDRITIC CELLS TO IMPROVE THEIR IMMUNOGENICITY

(71) Applicant: Julius-Maximilians-Universität Würzburg, Würzburg (DE)

(72) Inventors: Marion Heuer, Würzburg (DE); Manfred Lutz, Kürnach (DE); Andreas Beilhack, Würzburg (DE)

(73) Assignee: JULIUS-MAXIMILIANS-UNIVERSITÄT WÜRZBURG, Würzburg (DE)

( * ) Notice: Subject to any disclaimer, the term of this patent is extended or adjusted under 35 U.S.C. 154(b) by 153 days.

(21) Appl. No.: 15/106,082

(22) PCT Filed: Dec. 18, 2014

(86) PCT No.: PCT/EP2014/078447
§ 371 (c)(1),
(2) Date: Jun. 17, 2016

(87) PCT Pub. No.: WO2015/091787
PCT Pub. Date: Jun. 25, 2015

(65) Prior Publication Data
US 2016/0312184 A1 Oct. 27, 2016

(30) Foreign Application Priority Data

Dec. 18, 2013 (EP) .................... 13198153

(51) Int. Cl.
| | |
|---|---|
| *C12N 5/00* | (2006.01) |
| *C12N 5/02* | (2006.01) |
| *C12N 5/0784* | (2010.01) |
| *A61K 39/00* | (2006.01) |

(52) U.S. Cl.
CPC ........ *C12N 5/0639* (2013.01); *A61K 39/0011* (2013.01); *C12N 5/064* (2013.01); *A61K 2039/5154* (2013.01); *C12N 2501/02* (2013.01); *C12N 2501/2301* (2013.01); *C12N 2501/2306* (2013.01); *C12N 2501/25* (2013.01); *C12N 2501/71* (2013.01)

(58) Field of Classification Search
None
See application file for complete search history.

(56) References Cited

U.S. PATENT DOCUMENTS

| | | | |
|---|---|---|---|
| 6,383,498 B1 * | 5/2002 | Rhodes | A61K 39/39 424/204.1 |
| 2012/0039926 A1 | 2/2012 | Rosenthal et al. | |

FOREIGN PATENT DOCUMENTS

WO   WO 2011/006084 A2   1/2011

OTHER PUBLICATIONS

Zheng et al., 1992, Science vol. 256: 1560-1563.*
Nair et al., 2012, CUrr. Protoc, Immunol. 1-31.*
Strome et al., 2002, Can. Res. vol. 1884-1889.*
Novogrodsky et al., 1977, J. Immunol. vol. 118: 852-857.*
Henri et al., 2001, J. Immunol. vol. 167: 741-748.*
Dixon et al., 1976, J. Immunol. vol. 116: 575-578.*
Klinkert et al., 1980, PNAS, vol. 77: 5414-5418.*
Benencia, Fabian et al., "Dendritic Cells the Tumor Microenvironment and the Challenges for an Effective Antitumor Vaccination," *Journal of Biomedicine and Biotechnology*, Jan. 1, 2012, 7(8):Article ID 425476, pp. 1-15.
Cintolo, Jessica A. et al., "Dendritic cell-based vaccines: barriers and opportunities," *Future Oncology*, 2012, 8(10):1273-1299.

* cited by examiner

*Primary Examiner* — Amy E Juedes
(74) *Attorney, Agent, or Firm* — Saliwanchik, Lloyd & Eisenschenk

(57) ABSTRACT

The present invention relates to a method for producing dendritic cells with increased capability to activate T cells, to dendritic cells obtainable by such a method, and to a pharmaceutical composition comprising such dendritic cells.

7 Claims, 11 Drawing Sheets

Figures 1A, 1B:
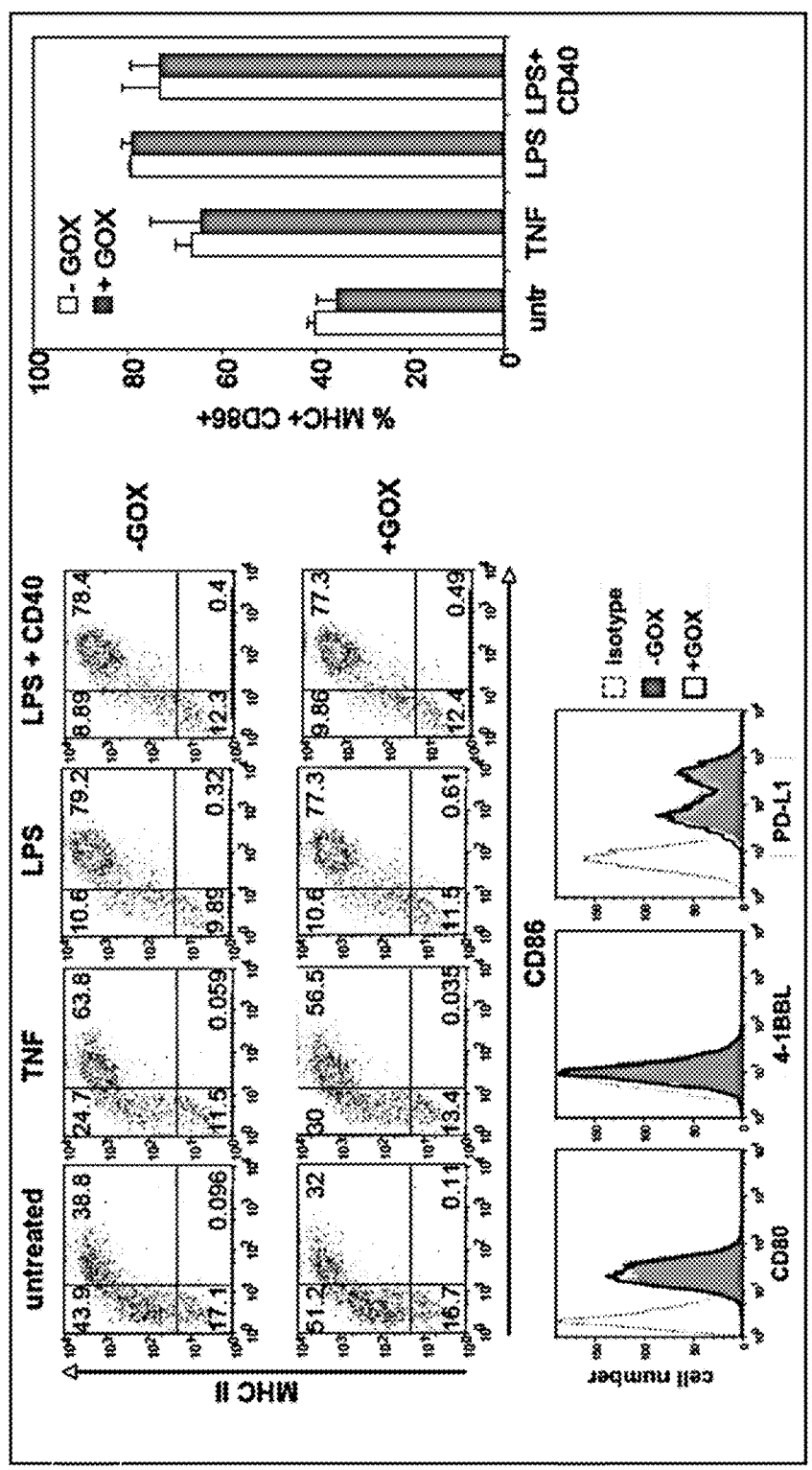

# GALACTOSE OXIDASE TREATMENT OF DENDRITIC CELLS TO IMPROVE THEIR IMMUNOGENICITY

CROSS REFERENCE TO RELATED APPLICATIONS

This application is a National Stage Application of International Application Number PCT/EP2014/078447, filed Dec. 18, 2014; which claims priority to European Application No. 13198153.2, filed Dec. 18, 2013; all of which are incorporated herein by reference in their entirety.

The present invention relates to a method for producing dendritic cells with increased capability to activate T cells, to dendritic cells obtainable by such a method, and to a vaccine or pharmaceutical composition comprising such dendritic cells.

Cancer immunotherapy seeks to harness the power and specificity of the immune system to treat tumors. One approach in cancer immunotherapy is through tumor vaccination, i.e. the provision of a tumor-specific antigen together with an adjuvant in order to elicit a T cell response against the tumor.

Dendritic cells (DCs) are the major cell type to induce primary T cell responses. Due to their properties, mature DCs are promising tools for immunogenic vaccination strategies against infectious diseases and tumors. Their maturation or activation is a critical step to acquire immunogenic capacity and is characterized by the upregulation of MHC (Major histocompatibility complex) and costimulatory molecules on the cell surface and secretion of cytokines.

DC maturation is the prerequisite to prime T cell responses. Various stimuli have been discovered to improve this potential and further search for factors improving the adjuvanticity of mature DCs is encouraged. Due to their potential to initiate adaptive immune responses, the injection of DCs represents a promising approach in vaccine development, and is currently tested in clinical studies especially to treat cancer.

The success of DC-mediated T cell priming depends on high levels of antigen presentation on MHC molecules (Signal 1), costimulatory molecules (Signal 2) and the secretion of soluble mediators and pro-inflammatory cytokines (Signal 3). In addition to these signals mostly discovered in vitro, the migration of antigen-loaded DCs to the T cell areas of secondary lymphoid organs is another hallmark of DC function and T cell priming prerequisite in vivo.

After arrival in the lymph node, DCs present antigen to T cells, and candidates with the appropriate TCR (T cell receptor) specificity for the presented antigen will, after initial tethering, form stable interactions with the DCs over periods lasting several hours. The firm DC/T cell interactions occur in multifocal synapses involving specific adhesion molecules of the immunoglobulin- and integrin-families and lead to pairings such as the LFA-1 integrin with its Ig superfamily ligand ICAM-1. Before such stable synapses can be formed, glycocalyx modifications are required to allow physical contact between cells and to optimize adhesion between both interaction partners during antigen presentation. Large and heavily glycosylated surface molecules such as CD43 and CD45 play major roles in initial cellular repulsion and thus need to be excluded from the later formed synapse. Thus, effective T cell activation during priming and repetitive stimulation of T cells by dendritic cells, depends on a close physical interaction between antigen presenting cells and T cells.

The past years have provided significant progress in the understanding of the molecular events underlying tumor vaccination with dendritic cells, and clinical trials have shown the general feasibility of the approach. However, successful application of this approach in the treatment of patients will still require substantial improvements in the procedure. Of particular importance will be to increase the efficiency with which dendritic cells activate T cells.

Thus, there is a need in the art for DCs for use in tumor vaccination that allow for activation of T cells with increased efficiency.

Preparation of a sufficient number of dendritic cells for vaccination is often difficult, time-intensive and costly. Hence, there is a need in the art for tumor vaccination approaches with DCs that are less time-intensive and less costly. Moreover, there is a need in the art for tumor vaccination strategies, which require less DCs, but are still effective.

Traditionally, preparing mature DCs with increased immunogenicity, i.e. with an increased capability to activate T cells, for tumor vaccination has been work- and cost-intensive, since additional preparation steps are necessary if not only steps for DC maturation, but also steps to increase the immunogenicity of the dendritic cells have to be included. Thus, there is a need in the art for ways to prepare mature DCs with increased immunogenicity that require fewer preparation steps.

One step in the preparation of dendritic cells for tumor vaccination that involves a significant investment of time, labor and cost is the maturation of dendritic cells. Thus, there is a need in the art for tumor vaccination approaches that can be carried out with immature DCs.

It is therefore an object of the present invention to provide for improved ways to produce dendritic cells, in particular dendritic cells for tumor vaccination. Moreover, it is an object of the present invention to provide for ways to generate dendritic cells for tumor vaccination with an increased capability to activate T cells. Moreover, it is an object of the present invention to provide for tumor vaccination approaches with DCs that are less time-intensive and/or less costly. Moreover, it is an object of the present invention to provide for dendritic cells for tumor vaccination strategies that enable tumor vaccination approaches, which require less DCs, but, preferably, are still effective. Furthermore, it is an object of the present invention to provide for ways to prepare mature DCs with increased immunogenicity that require fewer preparation steps. Moreover, it is an object of the present invention to provide for tumor vaccination approaches that can be carried out with immature DCs.

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

The objects of the present invention are solved by a method for producing dendritic cells with increased capability to activate T cells, wherein said method comprises the step of treating dendritic cells with galactose oxidase.

In one embodiment, said method is carried out in vitro. In one embodiment, said galactose oxidase treatment of the dendritic cells is carried out in vitro.

In one embodiment, said dendritic cells to be treated with galactose oxidase are mouse cells or human cells.

In one embodiment, said dendritic cells to be treated with galactose oxidase are non-human mammalian cells, preferably feline, canine, or equine cells.

In one embodiment, said dendritic cells to be treated with galactose oxidase are mature dendritic cells. Preferably, said mature dendritic cells have been obtained by treatment with one or several of
- one or a combination of agents selected from the group consisting of $PGE_2$, IL-6, TNF and IL-1β, preferably a combination of $PGE_2$, IL-6, TNF and IL-1β,
- one or a combination of agents selected from the group consisting of $PGE_2$, IL-6, TNF and IL-1β, preferably a combination of $PGE_2$, IL-6, TNF and IL-1β, in combination with CD40 stimulation, preferably by anti-CD40 antibody
- LPS
- LPS in combination with CD40 stimulation, preferably by anti-CD40 antibody
- a Toll-like receptor ligand, preferably Poly I:C In one embodiment, said galactose oxidase treatment of said dendritic cell is carried out before, during and/or after treatment of the dendritic cells with a maturation stimulus/maturation stimuli, wherein, preferably, said maturation stimulus is one or several of
- one or a combination of agents selected from the group consisting of $PGE_2$, IL-6, TNF and IL-1β, preferably a combination of $PGE_2$, IL-6, TNF and IL-1β,
- one or a combination of agents selected from the group consisting of $PGE_2$, IL-6, TNF and IL-1β, preferably a combination of $PGE_2$, IL-6, TNF and IL-1β, in combination with CD40 stimulation, preferably by anti-CD40 antibody
- LPS
- LPS in combination with CD40 stimulation, preferably by anti-CD40 antibody
- a Toll-like receptor ligand, preferably Poly I:C.

In one embodiment, said dendritic cells to be treated with galactose oxidase are immature dendritic cells and, preferably, are not exposed to any of
- one or a combination of agents selected from the group consisting of $PGE_2$, IL-6, TNF and IL-1β, preferably a combination of $PGE_2$, IL-6, TNF and IL-1β,
- one or a combination of agents selected from the group consisting of $PGE_2$, IL-6, TNF and IL-1β, preferably a combination of $PGE_2$, IL-6, TNF and IL-1β, in combination with CD40 stimulation, preferably by anti-CD40 antibody
- LPS
- LPS in combination with CD40 stimulation, preferably by anti-CD40 antibody
- a Toll-like receptor ligand, preferably Poly I:C.
- during or after treatment with galactose oxidase, more preferably are not exposed to any maturation stimulus during or after treatment with galactose oxidase.

In one embodiment, said dendritic cells are not treated with any maturation stimulus before, during or after treatment with galactose oxidase.

In one embodiment, said dendritic cells are not treated with neuraminidase before, during or after treatment with galactose oxidase. In one embodiment, said dendritic cells have not been and are not treated with neuraminidase before treatment with galactose oxidase. In one embodiment, said dendritic cells are not treated with neuraminidase during treatment with galactose oxidase. In one embodiment, said dendritic cells are not treated with neuraminidase after treatment with galactose oxidase.

In one embodiment, said dendritic cells with an increased capability to activate T cells are for use in dendritic cell-based vaccination of tumor patients, wherein, preferably, said tumor is a solid tumor or a liquid tumor. Preferably, said solid tumor is melanoma, breast cancer, prostate cancer, neuroblastoma, colon carcinoma or a cancer of the lung, brain, liver, thyroid, bone, adrenal, spleen, kidney, small intestine, pancreas, colon, stomach, endometrium, testicle, ovary, skin, head and neck, or esophagus, more preferably said solid tumor is melanoma, breast cancer, prostate cancer, neuroblastoma or colon carcinoma, more preferably said solid tumor is melanoma. Preferably, said liquid tumor is a leukemia, lymphoma or myeloma, more preferably said liquid tumor is a leukemia, more preferably said liquid tumor is AML (Acute myeloid leukemia) or CML (Chronic myelogenous leukemia).

In one embodiment, said dendritic cells to be treated with galactose oxidase present tumor antigens. In one embodiment, said dendritic cells with increased capability to activate T cells present tumor antigens. In one embodiment, the dendritic cells are loaded with tumor antigens before said treatment with galactose oxidase. In one embodiment, the dendritic cells are loaded with tumor antigens after said treatment with galactose oxidase.

In one embodiment, said dendritic cells with increased capability to activate T cells have an increased capability to activate T cells upon injection into a patient, compared to dendritic cells not treated with galactose oxidase, but otherwise treated in the same way.

In one embodiment, said dendritic cells with increased capability to activate T cells maintain their increased capability to activate T cells after administration to a patient.

In one embodiment, if, preferably, the dendritic cells to be treated with galactose oxidase are murine dendritic cells, said dendritic cells to be treated with galactose oxidase are obtained from bone marrow. In one embodiment, if, preferably, the dendritic cells to be treated with galactose oxidase are human dendritic cells, said dendritic cells to be treated with galactose oxidase are obtained from monocytes by in vitro differentiation. Preferably, said in vitro differentiation involves treatment with GM-CSF and human IL-4 and, preferably, one or more cytokines selected from the group consisting of TGF-beta, IL-34, IL-13 and M-CSF, or treatment with Flt3L and, preferably, one or more cytokines selected from the group consisting of TGF-beta, IL-34, IL-13 and M-CSF. In one embodiment, if, preferably, the dendritic cells to be treated with galactose oxidase are human dendritic cells, said dendritic cells are obtained from peripheral blood. Preferably, said obtaining dendritic cells from peripheral blood involves treatment with GM-CSF and human IL-4 and, preferably, one or more cytokines selected from the group consisting of TGF-beta, IL-34, IL-13 and M-CSF, or treatment with Flt3L and, preferably, one or more cytokines selected from the group consisting of TGF-beta, IL-34, IL-13 and M-CSF. In one embodiment, said dendritic cells to be treated with galactose oxidase are obtained from hematopoietic DC precursor or progenitor cells by in vitro differentiation.

In one embodiment, if, preferably, the dendritic cells to be treated with galactose oxidase are murine dendritic cells, preferably immature dendritic cells, the dendritic cells produced according to the invention show the same expression of MHC II, CD86, CD80, 4-1BBL and/or PD-L1 compared to immature murine dendritic cells not treated with galactose oxidase, but otherwise treated in the same way.

In one embodiment, if, preferably, the dendritic cells to be treated with galactose oxidase are murine dendritic cells, preferably immature dendritic cells, the dendritic cells produced according to the invention show the same level of secretion of IL-6 and/or IL-12 compared to immature murine dendritic cells not treated with galactose oxidase, but otherwise treated in the same way.

In one embodiment, said galactose oxidase treatment is for 1-5 hours, preferably 1-4 hours, more preferably 1-3 hours, more preferably 1-2 hours, more preferably about 90 minutes, at a concentration of 0.1-20 U/ml, preferably 0.5-10 U/ml, more preferably 1-5 U/ml, more preferably about 2 U/ml. In one embodiment, said galactose oxidase treatment is for 8-12 hours at a concentration of 0.1-20 U/ml, preferably 0.5-10 U/ml, more preferably 1-5 U/ml, more preferably about 2 U/ml.

Preferably, the galactose oxidase treatment of bone marrow-derived dendritic cells is carried out at a day within days 5-10 after obtaining the cells from the bone marrow, more preferably at day 8 after obtaining the cells from the bone marrow. Preferably, the galactose oxidase treatment of dendritic cells obtained from monocytes is carried out at a day within days 2-8, more preferably at day 5 or 6 after starting to differentiate said monocytes.

In one embodiment, if, preferably, the dendritic cells to be treated with galactose oxidase are immature murine dendritic cells and not treated with any maturation stimulus during or after galactose oxidase treatment, the dendritic cells produced according to the invention show an at least 2-fold, preferably at least 3-fold, more preferably at least 5-fold increase in their capability to activate T cells, compared to immature murine dendritic cells not treated with galactose oxidase, but otherwise treated in the same way. In one embodiment, if, preferably, the dendritic cells to be treated with galactose oxidase are immature murine dendritic cells and not treated with any maturation stimulus during or after galactose oxidase treatment, the dendritic cells produced according to the invention show an at least 2-fold, preferably at least 3-fold, more preferably at least 5-fold increase in their capability to activate T cells, compared to immature murine dendritic cells not treated with galactose oxidase and not treated with any maturation stimulus.

In one embodiment, if, preferably, the dendritic cells to be treated with galactose oxidase are immature murine dendritic cells and treated with maturation stimuli, preferably with one or several of
  one or a combination of agents selected from the group consisting of $PGE_2$, IL-6, TNF and IL-1β, preferably a combination of $PGE_2$, IL-6, TNF and IL-1β,
  one or a combination of agents selected from the group consisting of $PGE_2$, IL-6, TNF and IL-1β, preferably a combination of $PGE_2$, IL-6, TNF and IL-1β, in combination with CD40 stimulation, preferably by anti-CD40 antibody
  LPS
  LPS in combination with CD40 stimulation, preferably by anti-CD40 antibody
  a Toll-like receptor ligand, preferably Poly I:C
during or after galactose oxidase treatment, the dendritic cells produced according to the invention show an at least 1.5-fold, preferably at least 2-fold, more preferably at least 3-fold, more preferably at least 5-fold increase in their capability to activate T cells, compared to immature murine dendritic cells not treated with galactose oxidase, but otherwise treated in the same way.

In one embodiment, if, preferably, the dendritic cells to be treated with galactose oxidase are mature murine dendritic cells, the dendritic cells produced according to the invention show an at least 1.2-fold, preferably at least 1.4-fold, more preferably at least 1.6-fold, more preferably at least 1.8-fold, more preferably at least 2-fold increase in their capability to activate T cells, compared to mature murine dendritic cells not treated with galactose oxidase, but otherwise treated in the same way.

In one embodiment, if, preferably, the dendritic cells to be treated with galactose oxidase are immature human dendritic cells and not treated with any maturation stimulus during or after galactose oxidase treatment, the dendritic cells produced according to the invention show an at least 2-fold, preferably at least 3-fold, more preferably at least 5-fold, more preferably at least 8-fold, more preferably at least 10-fold increase in their capability to activate T cells, compared to immature human dendritic cells not treated with galactose oxidase, but otherwise treated in the same way.

In one embodiment, if, preferably, the dendritic cells to be treated with galactose oxidase are immature human dendritic cells and treated with maturation stimuli, preferably with one or several of
  one or a combination of agents selected from the group consisting of $PGE_2$, IL-6, TNF and IL-1β, preferably a combination of $PGE_2$, IL-6, TNF and IL-1β,
  one or a combination of agents selected from the group consisting of $PGE_2$, IL-6, TNF and IL-1β, preferably a combination of $PGE_2$, IL-6, TNF and IL-1β, in combination with CD40 stimulation, preferably by anti-CD40 antibody
  LPS
  LPS in combination with CD40 stimulation, preferably by anti-CD40 antibody
  a Toll-like receptor ligand, preferably Poly I:C
during or after galactose oxidase treatment, the dendritic cells produced according to the invention show an at least 2-fold, preferably at least 3-fold, more preferably at least 5-fold, more preferably at least 8-fold, more preferably at least 10-fold increase in their capability to activate T cells, compared to immature human dendritic cells not treated with galactose oxidase, but otherwise treated in the same way.

In one embodiment, if, preferably, the dendritic cells to be treated with galactose oxidase are mature human dendritic cells, the dendritic cells produced according to the invention show an at least 1.2-fold, preferably at least 1.4-fold, more preferably at least 1.6-fold, more preferably at least 1.8-fold, more preferably at least 2-fold increase in their capability to activate T cells, compared to mature human dendritic cells not treated with galactose oxidase, but otherwise treated in the same way.

In one embodiment of the activation assay, said capability to activate T cells, i.e. the dendritic cells' capability to activate T cells, is measured by an in vitro proliferation assay, preferably involving culturing the dendritic cells with syngeneic or allogeneic T cells or T cells specific for an antigen presented by said dendritic cell and measuring T cell proliferation by, preferably, determining incorporation of [$^3$H]-Thymidin or dilution of fluorescent dyes such as carboxyfluoresceinsuccinimidylester (CFSE). In one embodiment of the activation assay, said increased capability to activate T cells is measured by an in vivo T cell priming assay, preferably involving antigen-specific DC-based immunization followed by antigen-specific restimulation of T cells and then determining incorporation of [$^3$H]-Thymidin. Preferably, said in vivo T cell priming assay is carried out with T cells from peripheral blood, wherein, preferably, said T cells are obtained from peripheral blood after DC-based immunization and before restimulation of the T cells.

In one embodiment of the activation assay, allogeneic or syngeneic T cells are used in said proliferation assay.

In one embodiment of the activation assay, in said proliferation assay a preferential expansion of allogeneic over syngeneic T cells is observed with dendritic cells treated with galactose oxidase compared to dendritic cells not treated with galactose oxidase, but otherwise treated in the same way.

In one embodiment of the activation assay, if, preferably, the dendritic cells to be treated with galactose oxidase are murine dendritic cells, said increased capability to activate T cells is or is also observed with T cells obtained from lymph nodes and/or with T cells obtained from the spleen.

In one embodiment of the activation assay, said dendritic cells with an increased capability to activate T cells are capable of activating low affinity T cells, preferably low affinity tumor-specific T cell receptor bearing T cells.

In one embodiment, if, preferably, the dendritic cells to be treated with galactose oxidase are immature human dendritic cells and not treated with any maturation stimulus during or after galactose oxidase treatment, the dendritic cells produced according to the invention show significantly increased expression of the maturation markers HLA-DR, CD83, CD86 and/or CD25 compared to immature human dendritic cells not treated with galactose oxidase, but otherwise treated in the same way, wherein, preferably, said increase in CD25 expression is at least 10-fold, more preferably at least 50-fold, more preferably at least 80-fold, more preferably at least 100-fold, more preferably at least 200-fold, more preferably at least 300-fold, more preferably at least 400-fold, more preferably at least 500-fold, more preferably at least 600-fold compared to immature human dendritic cells not treated with galactose oxidase, but otherwise treated in the same way, and wherein, preferably, said increase in CD83 expression is at least 10-fold, more preferably at least 50-fold, more preferably at least 80-fold, more preferably at least 100-fold, more preferably at least 200-fold, more preferably at least 300-fold, more preferably at least 300-fold compared to immature human dendritic cells not treated with galactose oxidase, but otherwise treated in the same way.

In one embodiment, if, preferably, the dendritic cells to be treated with galactose oxidase are immature human dendritic cells and treated with maturation stimuli, preferably with one or several of one or a combination of agents selected from the group consisting of PGE$_2$, IL-6, TNF and IL-1β, preferably a combination of PGE$_2$, IL-6, TNF and IL-1β, one or a combination of agents selected from the group consisting of PGE$_2$, IL-6, TNF and IL-1β, preferably a combination of PGE$_2$, IL-6, TNF and IL-1β, in combination with CD40 stimulation, preferably by anti-CD40 antibody

LPS

LPS in combination with CD40 stimulation, preferably by anti-CD40 antibody a Toll-like receptor ligand, preferably Poly I:C during or after galactose oxidase treatment, the dendritic cells produced according to the invention show significantly increased expression of the maturation markers HLA-DR, CD83, CD86 and/or CD25 compared to immature human dendritic cells not treated with galactose oxidase, but otherwise treated in the same way, wherein, preferably, said increase in CD25 expression is at least 10-fold, more preferably at least 50-fold, more preferably at least 80-fold, more preferably at least 100-fold compared to immature human dendritic cells not treated with galactose oxidase, but otherwise treated in the same way, and wherein, preferably, said increase in CD83 expression is at least 10-fold, more preferably at least 50-fold, more preferably at least 80-fold, more preferably at least 100-fold compared to immature human dendritic cells not treated with galactose oxidase, but otherwise treated in the same way.

In one embodiment, if, preferably, the dendritic cells to be treated with galactose oxidase are mature human dendritic cells, the cells show significantly increased expression of the maturation markers HLA-DR, CD83, CD86 and/or CD25 compared to mature human dendritic cells not treated with galactose oxidase, but otherwise treated in the same way, wherein, preferably, said increase in HLA-DR expression is at least 10-fold, more preferably at least 50-fold, more preferably at least 80-fold, more preferably at least 100-fold compared to mature human dendritic cells not treated with galactose oxidase, but otherwise treated in the same way, wherein, preferably, said increase in CD83 expression is at least 10-fold, more preferably at least 50-fold, more preferably at least 80-fold, more preferably at least 100-fold compared to mature human dendritic cells not treated with galactose oxidase, but otherwise treated in the same way, wherein, preferably, said increase in CD86 expression is at least 10-fold, more preferably at least 50-fold, more preferably at least 80-fold, more preferably at least 100-fold compared to mature human dendritic cells not treated with galactose oxidase, but otherwise treated in the same way, and wherein, preferably, said increase in CD25 expression is at least 10-fold, more preferably at least 50-fold, more preferably at least 80-fold, more preferably at least 100-fold compared to mature human dendritic cells not treated with galactose oxidase, but otherwise treated in the same way.

Preferably, the expression of HLA-DR, CD83, CD86 and/or CD25 is measured by antibody staining and subsequent FACS analysis.

In one embodiment, if, preferably, the dendritic cells to be treated with galactose oxidase are immature human dendritic cells and not treated with any maturation stimulus during or after galactose oxidase treatment, the cells show increased release of IL-6, and IL-12p40, compared to mature human dendritic cells not treated with galactose oxidase, but otherwise treated in the same way, wherein, preferably, said increase in IL-6 is at least 50-fold, more preferably at least 100-fold, more preferably at least 200-fold, more preferably at least 300-fold, more preferably at least 400-fold, more preferably at least 500-fold, more preferably at least 800-fold, more preferably at least 1000-fold, more preferably at least 1500-fold, more preferably at least 2000-fold, more preferably at least 2500-fold to immature human dendritic cells not treated with galactose oxidase, but otherwise treated in the same way, and wherein, preferably, said increase in IL-12p40 release is at least 2-fold, more preferably at least 5-fold, more preferably at least 10-fold, and wherein, preferably, said increase in IL-12p40 release is below 10-fold, more preferably below 5 fold, more preferably below 2 fold.

In one embodiment, if, preferably, the dendritic cells to be treated with galactose oxidase are immature human dendritic cells and treated with maturation stimuli, preferably with one or several of
- one or a combination of agents selected from the group consisting of PGE$_2$, IL-6, TNF and IL-1β, preferably a combination of PGE$_2$, IL-6, TNF and IL-1β,
- one or a combination of agents selected from the group consisting of PGE$_2$, IL-6, TNF and IL-1β, preferably a combination of PGE$_2$, IL-6, TNF and IL-1β, in combination with CD40 stimulation, preferably by anti-CD40 antibody
- LPS
- LPS in combination with CD40 stimulation, preferably by anti-CD40 antibody
- a Toll-like receptor ligand, preferably Poly I:C
- during or after galactose oxidase treatment, the dendritic cells produced according to the invention show increased release of IL-6, but only marginally increased release of IL-12p40, compared to immature human dendritic cells not treated with galactose oxidase, but otherwise treated in the same way, wherein, preferably, said increase in IL-6 release is at least 10-fold, more preferably at least 50-fold, more preferably at least 100-fold, more preferably at least 200-fold, more preferably at least 300-fold compared to immature human dendritic cells not treated with galactose oxidase, but otherwise treated in the same way, and wherein, preferably, said increase in IL-12p40 release is at least 2-fold, more preferably at least 5-fold, more preferably at least 10-fold, and wherein, preferably, said increase in IL-12p40 release is below 10-fold, more preferably below 5 fold, more preferably below 2 fold.

Preferably, the release of IL-6 and/or IL-12p40 is measured by ELISA.

In one embodiment, if, preferably, the dendritic cells are murine cells and, preferably, the dendritic cells are reintroduced into a patient, preferably a human or a mouse, said dendritic cells with an increased capability to activate T cells migrate to the secondary lymphoid organs, preferably in lymph nodes, more preferably the popliteal and inguinal lymph nodes, and/or the spleen, in vivo with the same efficiency as dendritic cells not treated with galactose oxidase, but otherwise treated in the same way.

Preferably, migration to the secondary lymphoid organs is determined by labeling of DCs with a fluorescent dye and subsequent analysis by FACS analysis (mouse) or labeling of DCs with radioactive reagents (mouse and human) or loading of DCs with paramagnetic iron particles and analysis by Magnetic Resonance Imaging (mouse and human).

The objects of the present invention are also solved by a dendritic cell obtainable by the method for producing dendritic cells with increased capability to activate T cells as defined above or by any of the above-defined embodiments of this method.

In one embodiment, said dendritic cell is for use in vaccination, preferably in tumor vaccination, more preferably in tumor vaccination against a solid tumor or a liquid tumor. Preferably, said solid tumor is melanoma, breast cancer, prostate cancer, neuroblastoma, colon carcinoma or a cancer of the lung, brain, liver, thyroid, bone, adrenal, spleen, kidney, small intestine, pancreas, colon, stomach, endometrium, testicle, ovary, skin, head and neck, or esophagus, more preferably said solid tumor is melanoma, breast cancer, prostate cancer, neuroblastoma or colon carcinoma, more preferably said solid tumor is melanoma. Preferably, said liquid tumor is a leukemia, lymphoma or myeloma, more preferably said liquid tumor is a leukemia, more preferably said liquid tumor is AML (Acute myeloid leukemia) or CML (Chronic myelogenous leukemia).

In one embodiment, said dendritic cell is administered to a patient. Preferably, an effective amount of said dendritic cells is administered to a patient.

Preferably, said patient is a mammal, more preferably a mouse or a human being. Preferably, said patient is a non-human mammal, preferably a cat, dog or horse. Most preferably, said patient is a human being.

In one embodiment, said administration occurs by a series of injections, preferably by a series of at least 5, more preferably by a series of at least 10 injections. Preferably, said administration occurs by a series of not more than 10 injections, preferably by a series of not more than 5 injections. In one embodiment, 4-10 million dendritic cells are injected in each injection. In one embodiment, up to 4 million dendritic cells, preferably up to 2 million dendritic cells, more preferably up to 1 million dendritic cells, more preferably up to 0.5 million dendritic cells are injected in each injection.

In one embodiment, said administration occurs by injection, preferably by intravenous, subcutaneous or intradermal injection, more preferably by intravenous injection.

In one embodiment, said dendritic cell has an improved capability to activate T cells in vitro and in vivo compared to dendritic cells not treated with galactose oxidase, but otherwise treated in the same way.

In one embodiment, said dendritic cell has not been exposed to any maturation stimulus.

The objects of the present invention are also solved by a vaccine or a pharmaceutical composition comprising dendritic cells as defined in the embodiments above or a dendritic cell produced according to the method for producing dendritic cells with increased capability to activate T cells as defined in the embodiments above.

The objects of the present invention are also solved by galactose oxidase for use in the production of dendritic cells for tumor vaccination.

Preferably, in such use, said dendritic cells, said production of dendritic cells, said tumor and said tumor vaccination are as described in the embodiments above.

The objects of the present invention are also solved by a method for treatment of a patient who is suffering from a tumor, said method comprising the steps:
- obtaining a dendritic cell as defined in the embodiments above or a dendritic cell produced according to the method for producing dendritic cells with increased capability to activate T cells as defined in the embodiments above,
- administering said dendritic cell to said patient.

Preferably, in such method for treatment, said patient, said tumor, said tumor vaccination and said administering said dendritic cell to said patient are as described in the embodiments above.

The objects of the present invention are also solved by a method of using a dendritic cell as defined in the embodiments above or a dendritic cell produced according to the method for producing dendritic cells with increased capability to activate T cells as defined in the embodiments above for vaccinating a patient who is suffering from a tumor against said tumor.

Preferably, in such method of using a dendritic cell, said patient, said tumor and said vaccinating are as described in the embodiments above.

The objects of the present invention are also solved by the use of a dendritic cell as defined in the embodiments above or a dendritic cell produced according to the method for producing dendritic cells with increased capability to activate T cells as defined in the embodiments above for the manufacture of a medicament or a vaccine or a pharmaceutical composition for vaccinating a patient who is suffering from a tumor against said tumor.

In such use, said patient and said tumor are as described in the embodiments above.

"Dendritic cells" (DCs) are specialized antigen/presenting cells that are involved in initiating immune responses and maintaining tolerance of the immune system to self antigens (see, e.g., K. Murphy, P. Travers and M. Walport, "Janeway's Immunobiology", 7th ed., Garland Science, New York). Dendritic cells can be obtained from murine fetal liver, murine and human bone marrow, lymphatic organs such as the spleen or from various blood cells by in vitro differentiation with GM-CSF alone or GM-CSF plus IL-4, or IL-3 (1) or Flt3L, or GM-CSF plus Flt3L combinations. Additional factors such as SCF, TNF, CD40 ligand, IL-13, or TGF-beta may modify the subset or phenotype or enhance the number of cells generated but do not work alone for DC generation DCs can be generated from any hematopoietic progenitor cells, preferably from CD34+ cells present in peripheral blood, cord blood or lymphatic organs or monocytes from peripheral blood of mice and humans (2, 3).

Dendritic cells occur in an "immature" and in a "mature" state. The term "immature", as used herein in the context of "immature" dendritic cells, refers to a non-activated state of dendritic cells characterized by high rate of antigen uptake but low antigen presentation, low costimulation, low cytokine production and absence of lymph node homing capacity via CCR7. The term "mature", as used herein in the context of "mature" dendritic cells, refers to an activated state of dendritic cells characterized by reduced antigen uptake, high antigen presentation, high costimulation and high cytokine production as well as the lymph node homing capacity via CCR7. Further details about methods to distinguish mature from immature dendritic cells can be found in (4). "Maturation" of dendritic cells is the transition of a dendritic cell from the immature to the mature state and is a critical step to acquire immunogenic capacity. Typically, maturation of dendritic cells involves an increase in the expression of certain gene/molecules called "maturation markers", for example MHC II, CD86, CD80 and/or CD40 in murine dendritic cells, or HLA-DR, CD83, CD86 and/or CD25 in human dendritic cells. The expression level of such maturation markers can be determined by antibody staining and FACS (fluorescence activated cell sorting) analysis. Moreover, maturation of dendritic cells typically involves an increase in the secretion of certain cytokines, such as IL-6 and/or IL-12 (IL=interleukin). Such an increase in the secretion of cytokines can be determined by ELISA (enzyme-linked immunosorbent assay; IL-12 can be detected by an ELISA against the IL-12 subunit IL-12p40).

The term "maturation stimulus", as used herein, is meant to designate an agent that induces maturation of dendritic cells. DC maturation is the prerequisite to prime T cell responses. Various stimuli have been discovered to improve this potential and further search for factors improving the adjuvanticity of mature DCs is encouraged. Maturation stimuli are, for example, $PGE_2$ (prostaglandin E2), TNF (tumor necrosis factor), IL-6 (interleukin 6) and/or IL-1β (interleukin 1β); LPS (lipopolysaccharide); combinations of such factors, for example a combination of $PGE_2$, IL-6, TNF and IL-1β; such a factor or a combination of such factors in combination with an anti-CD40 antibody; LPS alone or in combination with an anti-CD40 antibody; or Poly I:C (polyinosinic:polycytidylic acid). The term, as used herein, does not include galactose oxidase, even though galactose oxidase causes maturation of human dendritic cells, as shown in this application.

The term "activate" or "activation" as used herein in relation to T cells refers to inducing a change in the biologic state of T cells by which the cells express activation markers, produce cytokines, proliferate and/or become cytotoxic to target cells. The term includes the term "priming" and, preferably one or both of the terms "restimulation" and "memory response" as used in the literature in relation to T cells.

At some instances, the present application refers to a dendritic cell having an "increased capability to activate T cells". This means that a certain number of dendritic cell of this kind can activate more T cells than the same number of dendritic cells with a lower capability to activate T cells can activate under the same conditions. The capability to activate T cells can be determined by an in vitro proliferation assay, which may involve culturing the dendritic cells with naive T cells and measuring T cell proliferation by, e.g., determining incorporation of [$^3$H]-Thymidin. Alternatively, T cells can be primed in vivo, then the T cells are isolated from blood (or, in mice, from spleen or lymph nodes), cultured with the dendritic cells, restimulated with antigen, and T cell proliferation is measured by, e.g., determining incorporation of [$^3$H]-Thymidin.

At some instances, a dendritic cell is said to have an "improved capability to activate T cells in vitro". This refers to a situation where an improved capability to activate T cells is observed with a dendritic cell in an in vitro assay. At some instances, a dendritic cell is said to have an "improved capability to activate T cells in vivo". This refers to a situation where an improved capability to activate T cells is observed with a dendritic cell in an in vitro assay.

The term "low affinity T cells", as used herein, refers to T cells that have undergone thymic selection for self-antigens where self-specific T cells with high affinity are depleted. The term "low affinity tumor-specific T cell receptor bearing T cells", as used herein, refers to T cells that recognize tumor antigens that represent self-antigens (e.g. overexpressed antigens) and have undergone thymic selection.

A "precursor cell", as used herein, refers to a partially differentiated cell having the capacity of undergoing further differentiation into a certain cell type or to acquire the capacity to perform a specific function. In contrast to a progenitor cell, a precursor cell requires only one or few differentiation steps to become a dendritic cell such as a monocyte. A "dendritic cell precursor cell" is a cell having the capacity of undergoing differentiation into a dendritic cell. A "hematopoietic dendritic cell precursor cell" is a cell which is derived from a hematopoietic stem cell and which has the capacity of undergoing differentiation into a dendritic cell.

A "progenitor cell", as used herein, refers to a partially differentiated cell having the capacity of undergoing further differentiation into a certain cell type or to acquire the capacity to perform a specific function. In contrast to a precursor cell, a progenitor cell requires several differentiation steps to become a dendritic cell such as a hematopoietic stem cell. A "dendritic cell progenitor cell" is a cell having the capacity of undergoing differentiation into a dendritic cell. A "hematopoietic dendritic cell progenitor cell" is a cell which is derived from a hematopoietic stem cell and which has the capacity of undergoing differentiation into a dendritic cell.

The term "galactose oxidase" (abbreviated "GOX") refers to an enzyme, preferably an enzyme with E.C. number 1.1.3.9, that catalyzes the selective oxidation of a primary hydroxyl group of galactose (Gal) and acetylated galactosamine (Gal-NAc) to their corresponding aldehydes.

The term "neuraminidase" (abbreviated "NA") refers to an enzyme, preferably an enzyme with E.C. number 3.2.1.18, that catalyzes the cleave of glycosidic linkages formed by neuraminic acids. The term also includes homologs of such enzymes in bacteria.

The phrase "treat", "treating" or "treatment", as used herein for example in the context of "treating" a dendritic cell with a certain agent or compound or "treatment" of a dendritic cell with a certain agent or compound, designates a situation where an effective amount of said agent or compound is brought into contact with said dendritic cell and allowed to act on said dendritic cell for a time span sufficient to bring about desired changes in said dendritic cell or its molecular components. For example, "treating" a dendritic cell with galactose oxidase refers to a situation where an effective amount of galactose oxidase is brought into contact with a dendritic cell and left in contact with said dendritic cell until changes in the oxidation state of galactose and/or galactoseamine molecules present on the surface of the dendritic cell have occurred.

As used herein, the term "in vitro" means occurring outside of a living organism. In contrast thereto, the term "in vivo" means occurring within a living organism. In vitro can describe processes and conditions occurring within a cell culture system. Where the application refers to a method comprising the step of treating dendritic cells with galactose oxidase being carried out in vitro, this is meant to designate that said dendritic cells are treated with galactose oxidase in a cell culture system outside of a living organism.

The term "dendritic cells to be treated with galactose oxidase", as used herein, refers to dendritic cells that are used as starting material for producing the dendritic cells with increased capability to activate T cells according to the invention. The term can refer to immature dendritic cells, mature dendritic cells, or a mixture of both kinds of dendritic cells.

The term "present", as used herein in the context of a dendritic cell "presenting" a certain antigen, is meant to designate a situation in which said antigen is bound to MHC molecules at the surface of said dendritic cell and is accessible for T cells. Loading of MHC class I or II molecules can be achieved by co-incubation of DCs with the protein or peptide antigen, e.g. for 1, 4 or 16 hours, or cytoplasmic targeting of the antigen as protein or peptide or mRNA or DNA e.g. by electroporation or viral vectors. Similarly, loading of tumor-glycolipids on CD1 molecules may be performed to activate NKT cells or loading of tumor antigens (protein or glycolipids) can lead to their regurgitation and exposure to B cells. In all cases T cells, NKT cells and B cells will be activated in antigen-specific manner. Activation can be determined by upregulation of activation markers such as CD69 detected e.g. by FACS analysis or cell proliferation detected as [$^3$H]-thymidin incorporation.

As used herein, the term "tumor vaccination" relates to a procedure in which immune responses directed against tumor cells are induced by introduction of dendritic cells loaded with tumor-specific antigens into a patient.

The term "tumor antigen", as used herein, designates an antigen with an amino acid sequence that is identical with the sequence or with part of the sequence of a protein, polypeptide or peptide or glycolipid that is expressed by a tumor cell. Preferably, such a tumor antigen is capable of being presented on MHC or CD1 molecules and, in combination with other signals, of inducing or activating tumor-specific T helper and cytotoxic T cells or NKT cells.

The term "syngeneic" in the context of "syngeneic" T cells being expanded in a T cell proliferation assay using dendritic cells refers to T cells from the same individual and thus with the same genetic background as the dendritic cells. In contrast, the term "allogeneic" in the context of "allogeneic" T cells being expanded in a T cell proliferation assay using dendritic cells refers to T cells from a different individual and thus with a different genetic background than the dendritic cells.

At some instances, the present application states that certain dendritic cells migrate to secondary lymphoid organs in vivo with the same efficiency as other cells. This means that, when an equal amount of both kinds of dendritic cells are injected into the body of a patient, after a certain time span, for example 5-30 minutes after intravenous injection in the spleen or 8-24 hours after subcutaneous injection in the lymph nodes, the same number of cells of both types of cells is observed in secondary lymphoid organs, such as the lymph nodes or the spleen. This can be measured by labeling of DCs with fluorescent dyes and subsequent analysis by FACS analysis (mouse) or labeling of DCs with radioactive reagents (mouse and human) or loading of DCs with paramagnetic iron particles and analysis by Magnetic Resonance Imaging (mouse and human).

The term "patient who is suffering from a tumor", as used herein, refers to a subject who has been tested and found to have tumor cells in his/her/its body. The presence of tumor cells may be diagnosed using any suitable method, including but not limited to, biopsy, x-ray, blood test, etc.

The present inventors have surprisingly found that treatment of murine and human DCs with galactose oxidase (GOX) alone or in addition to maturation stimuli further improves their capability to activate T cells in vitro and in vivo. Moreover, the present inventors have found that GOX treatment of immature human DCs induces their maturation, even in the absence of any maturation stimuli, and that DCs matured in this manner are highly capable of activating T cells.

The use of a combination of neuraminidase and galactose oxidase has been known as one of various treatments to stimulate lymphocyte proliferation. In these assays the sequential use of first neuraminidase and second GOX was required to stimulate T cell proliferation as responders within bulk peripheral blood cells, whereas the single components had no significant effects. Later it has been shown that the neuraminidase/GOX combination stimulated murine, rabbit and canine DCs, which then could improve T cell priming capability in vitro.

As the underlying mechanism of this treatment Schiff base formation between carbonyl groups on the presenting cell and amines on the T cell surface was found. GOX enzymatic activity catalyzes oxidation of R—$CH_2$—OH groups, such as at the $C_6$ position of galactose, into aldehydes R—CH=O and some other similar reactions. These aldehydes can then react with amines to form Schiff bases, that represent covalent bonds which can be formed intermolecularly in the same cell or intercellularly.

Neuraminidase/GOX was successfully used as an adjuvant against HIV peptides. Later, Schiff base forming pharmacologicals such as tucaresol, which substitute for the presenting cells as a carbonyl donor, were found to act as adjuvants and went to a clinical phase I/II study for HIV vaccination.

However, whether DC treatment with GOX alone would be effective on human DCs or would maintain its stimulatory effect on murine DCs also after their injection, remained open.

The inventors have treated murine bone-marrow derived DCs and human monocyte-derived DCs with GOX and tested their maturation as measured by surface markers and cytokine secretion as well as their T cell stimulation capability. While murine DCs remained unaffected by GOX with respect to their surface markers and cytokines, they nevertheless stimulated primary T cell responses much better in vitro and in vivo. In contrast, human DCs readily upregulated surface maturation markers and cytokine production with GOX alone and acted synergistically with other maturation stimuli. GOX treatment of human immature and mature DCs, generated under GMP conditions, improved T cell priming in vitro.

Although GOX alone only matures human but not mouse DCs as measured by surface markers and cytokine production, both human and mouse DCs improved their T cell priming capability in vitro, and, as shown for the murine cells, in vivo. Moreover, GOX treatment further improved the T cell priming of already matured DCs.

The chemical modification of glycosylated homing receptors on DCs by GOX may alter their homing potential. Homing of subcutaneously injected mature DCs to the draining lymph node, is however a prerequisite for successful T cell priming. In this study GOX-treated murine DCs further improved the T cell priming capability after subcutaneous DC injection, which indicates that negative impact on DC migration is not obtained by GOX treatment.

The fact that also syngeneic T cell proliferation was increased by GOX-treated DCs may indicate the activation of autoreactive T cells, which seems to appear as an unwanted response in vaccine strategies. However, in DC-based vaccines against tumors this might be even advantageous, since many tumor antigens are simply overexpressed but not mutated. In such settings the activation of low affinity autoreactive TCR (T cell receptor) bearing T cells would further improve the anti-cancer vaccine.

Together, the data presented in this application suggest additional GOX treatment of already matured DCs as a tool to further improve their T cell priming capacities. This additional adjuvant effect on top of classical DC maturation is expected to improve DC-vaccine approaches in tumor patients.

Tumor vaccination with dendritic cells typically comprises the following steps:

1. Selection of Tumor Antigens:

A substantial number of tumor antigens have been identified, including the protein/peptide antigens BAGE, MAGE, GAGE, NY-ESO-1, SSX, Gp100, Melan A/Mart-1, Tyrosinase, PSA, CEA, Mammaglobin A, p53, HER-2/neu, livin, survivin, β-Catenin-m, β-Actin/4/m, Myosin-m, HSP-70-2/m, HLA-A2-R170J but also carbohydrate antigens GM2, GD2, GD3, MUC-1, sTn, globo-H, and many of them can be and are currently used in DC-based anti-tumor vaccines (5).

2. Loading of DCs with Tumor Antigens:

Loading of MHC class I or II molecules can be achieved by co-incubation of DCs with the protein or peptide antigen, e.g. for 1, 4 or 16 hours or whole tumor lysates or cytoplasmic targeting of the antigen as protein or peptide or mRNA or DNA e.g. by electroporation or viral vectors or by nanoparticles. Similarly, loading of tumor-glycolipids on CD1 molecules may be performed to activate NKT cells or loading of tumor antigens (protein or glycolipids) can lead to their regurgitation and exposure to B cells for antibody production (6). In all cases T cells, NKT cells and B cells will be activated in antigen-specific manner. Activation can be determined by upregulation of activation markers such as CD69 detected e.g. by FACS analysis or cell proliferation detected as [$^3$H]-thymidin incorporation.

3. Maturation of DCs

Maturation can be achieved by exposing DCs to a maturation stimulus as described above (see paragraph defining the term "maturation stimulus").

DCs represent highly versatile sensors of the immune system to detect alterations in tissues that can harm the individual. For this DC express receptors for PAMPs (=pathogen associated molecular patterns) to identify microbial organisms, or receptors detecting tissue damage (DAMPs=danger associated molecular patterns), but also inflammation (inflammasome activation) as a secondary signal for changes in tissue integrity. Contact to either of these signals will change the genetic program of immature DCs. Major alterations include a switch from antigen recognition and uptake to antigen transport and presentation. Hallmarks of DC maturity are the upregulation of the surface molecules MHC I and II, CD80, CD86, CD83, CD40, CCR7 and CD25. Depending on the strength of stimulation or the type of pathogen DC will produce different types of cytokines such as IL-6 and/or IL-12 (7)

4. Injection of Patients

DC vaccinations are performed repetitively and mostly by injection of $4\text{-}10 \times 10^6$ cells each injection via intradermal, subcutaneous, intravenous, intralymphatic, intranodal, or intratumoral routes. Intradermal or subcutaneous routes appear advantageous since intravenous injection of the same type of DCs can turn out in unwanted tolerogenicity (8).

In the following, reference is made to the figures:

All methods mentioned in the figure descriptions below were carried out as described in detail in the examples.

FIGS. 1A-1B show experimental data addressing the question whether GOX treatment alters the expression of MHC II, CD86, CD80, 4-1BBL or PD-L1.

1A. Murine BM-DCs (bone-marrow derived dendritic cells) were generated until day 8, treated with GOX for 90 min, washed and matured overnight with TNF, LPS or LPS+anti-CD40. Then FACS analysis was performed for the indicated markers. Representative dot plots (left) and statistical evaluation as bar graphs (right) are shown. As is evident from the data, murine BM-DCs treated with GOX do not show altered expression of MHC II or CD86.

1B. Also, GOX treatment of immature DCs for 90 min and culture overnight does not alter CD80, 4-1BBL or PD-L1 expression as shown by FACS analysis.

All experiments shown are representative for three independent experiments with similar results.

Figure 2:
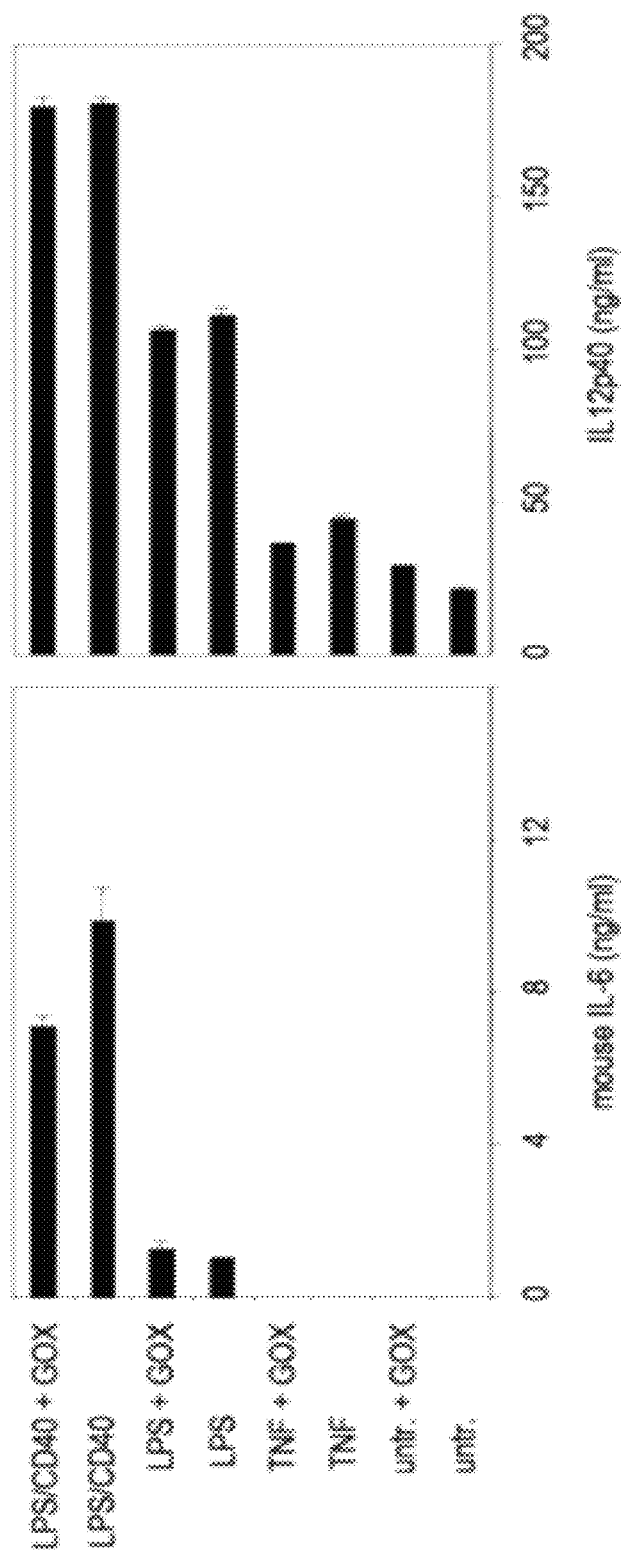

FIG. 2 shows experimental data addressing the question whether GOX treatment of murine BM-DCs leads to an increase in cytokine production of these cells.

BM-DCs were treated at day 8 for 90 min with GOX, washed and subsequently matured with the indicated stimuli overnight before IL-6 and IL-12p40 analysis by ELISA. The data are representative for three independent experiments with similar results.

As the data shows, GOX treatment of murine BM-DCs does not lead to an increase in cytokine release by these cells.

Figure 3A:
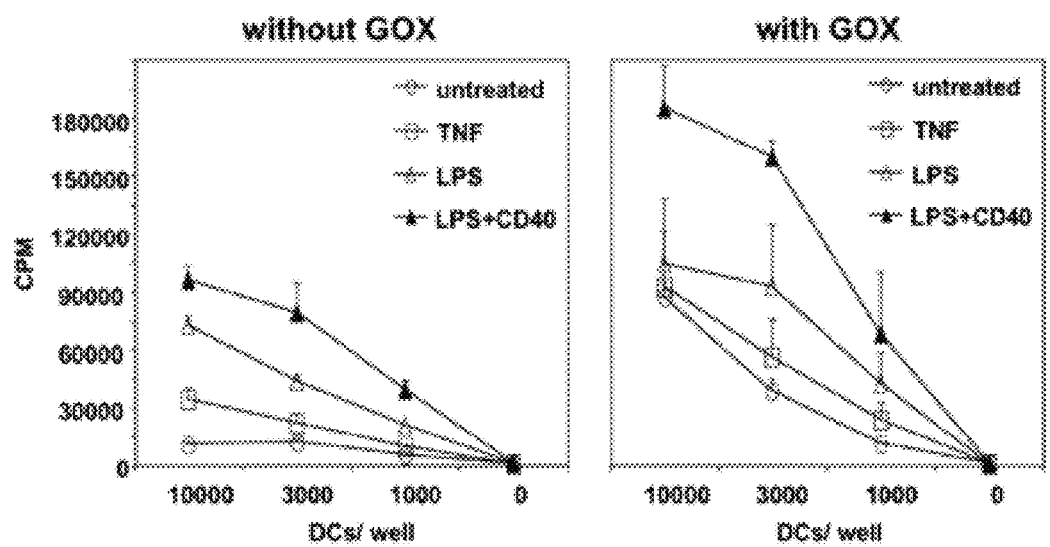
Figure 3B:
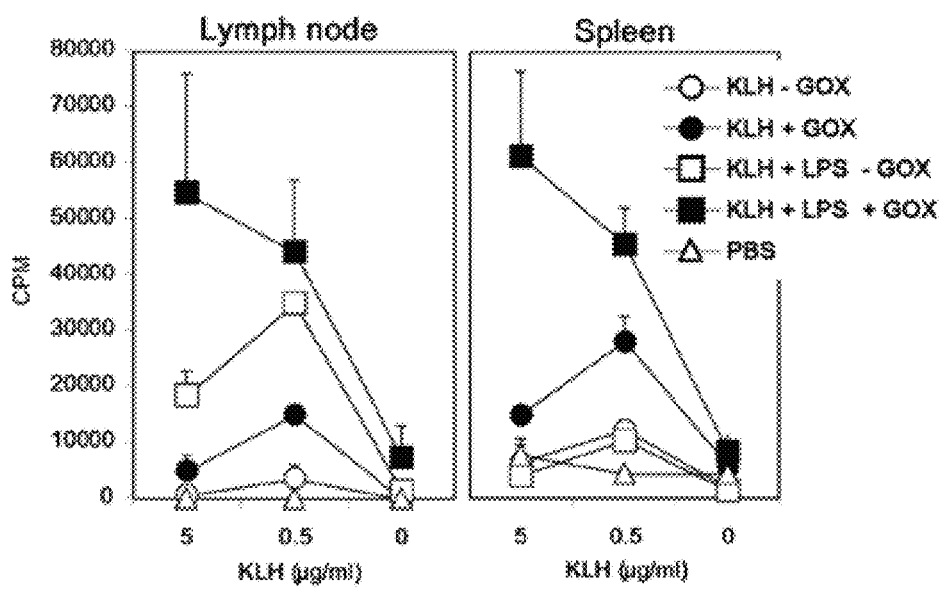

FIGS. 3A-3B show experimental data addressing the question whether immature and mature murine BM-DCs show increased T cell priming capability in vitro and in vivo after GOX treatment.

BM-DCs were generated until day 8, treated with GOX for 90 min and matured as indicated overnight.

3A. Then allogeneic lymph node cells were added as responder T cells for 3 days before proliferation was measured by [$^3$H]-thymidine incorporation.

3B. For in vivo priming the DCs were additionally loaded with KLH (keyhole limpet hemocyanin) antigen together with the maturation stimuli for 16 h and before GOX treatment. Then the DCs were washed and injected s.c. into syngeneic mice. After 11 days lymph nodes and spleen were restimulated with KLH and pulsed with [$^3$H]-thymidine to detect antigen-specific T cell priming. CPM=counts per minute. The data are representative for three independent experiments with similar results.

Thus, immature and mature murine BM-DCs show increased T cell priming capability in vitro and in vivo after GOX treatment.

Figure 4A:
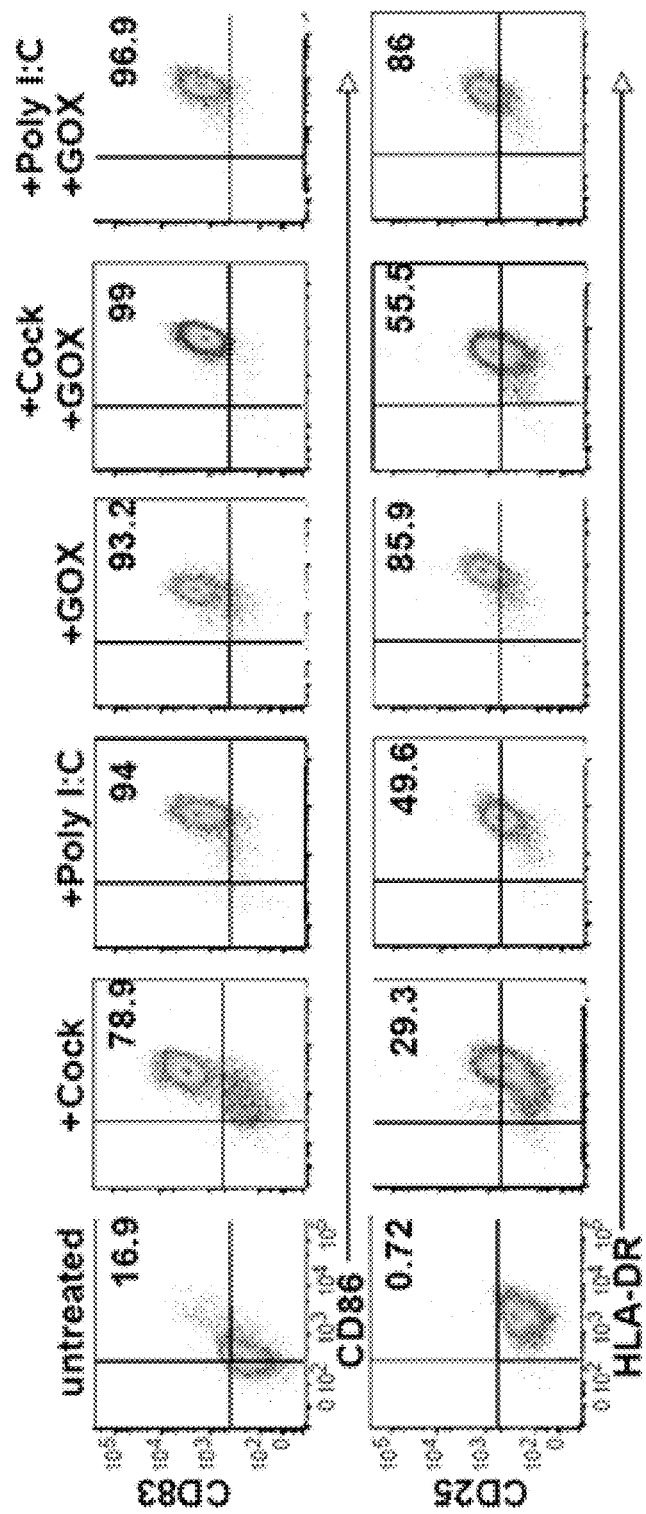
Figure 4B:
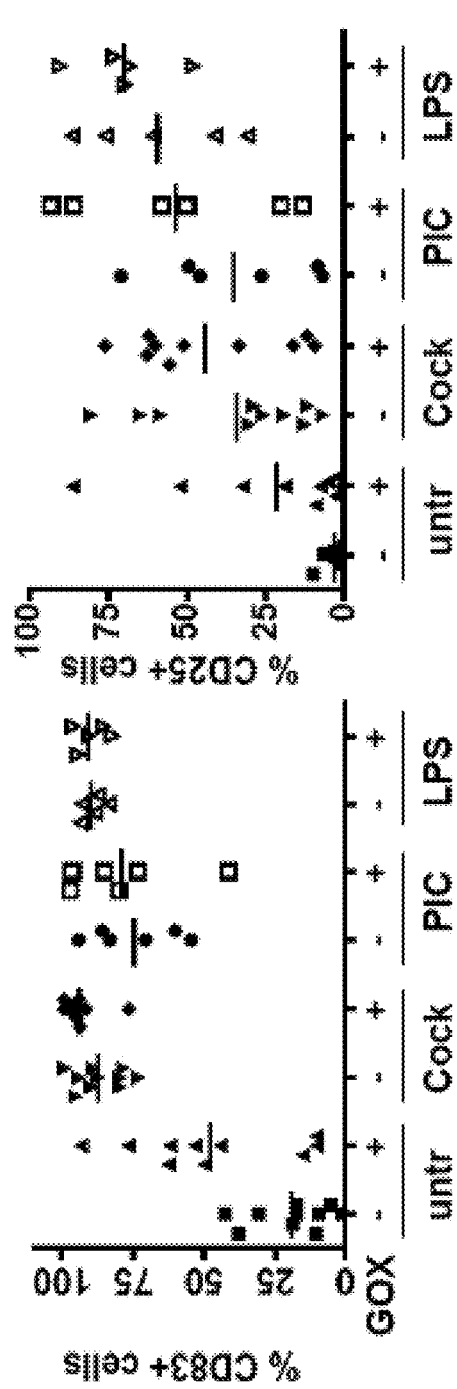
Figure 4C:
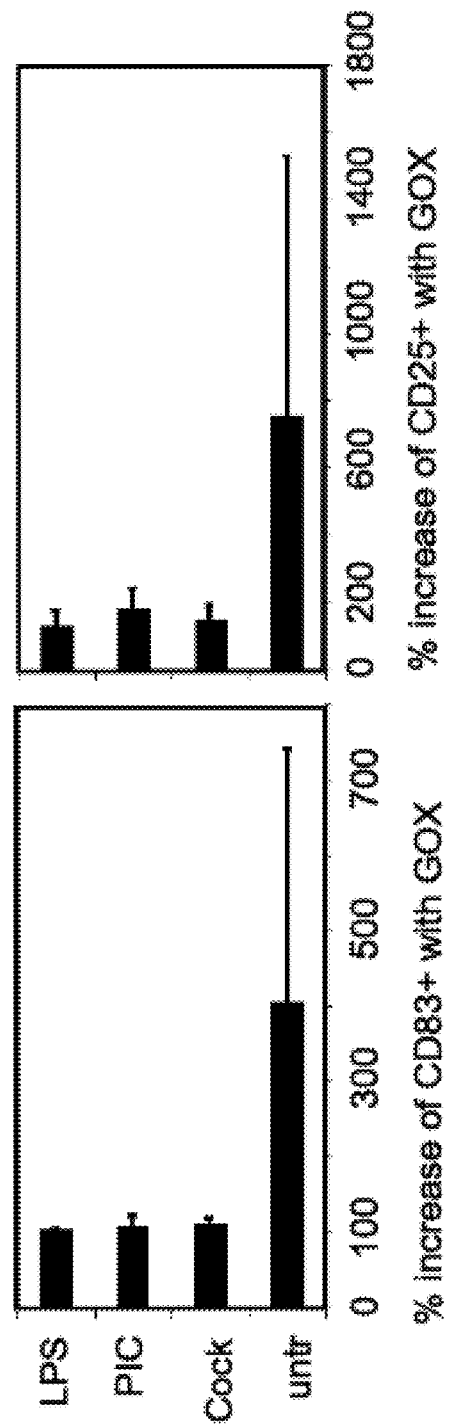

FIGS. 4A-4C show experimental data addressing the question whether human DCs mature by GOX treatment alone.

Human DCs were generated from monocytes and treated with different maturation stimuli or GOX or their combination overnight.

4A. Then cells were analyzed by FACS for surface marker expression as indicated from one representative donor.

4B. The results of FACS analyses of the CD83 and CD25 maturation markers of DCs from different donors are displayed (PIC=Poly I:C). Each data point represents the cytokine release of one donor±GOX treatment.

4C. The results from B were expressed as % increase of GOX-treated versus untreated cells. Thus, human DCs mature by GOX treatment alone.

Figures 5A, 5B:
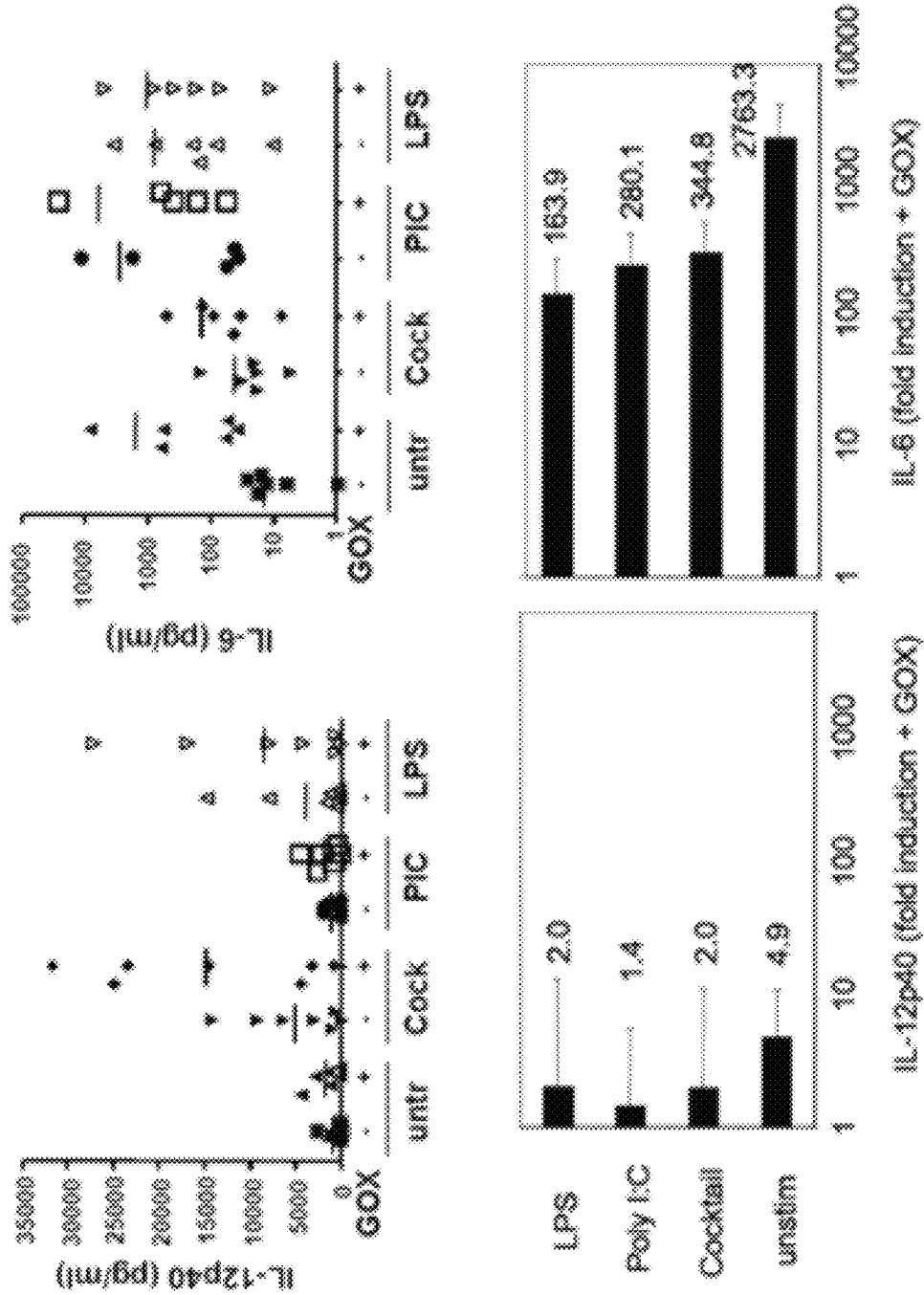

FIGS. 5A-5B show experimental data addressing the question whether GOX treatment causes increased IL-6 production of human DCs.

Human DCs were generated from monocytes and treated with different maturation stimuli or GOX or their combination overnight.

5A. Then the culture supernatants were tested by ELISA for their cytokine content.

5B. The results from A were expressed as fold increase of GOX-treated versus untreated cells. Each data point represents the cytokine release of one donor±GOX treatment.

Thus, GOX treatment heavily increases IL-6 production of human DCs.

Figure 6B:
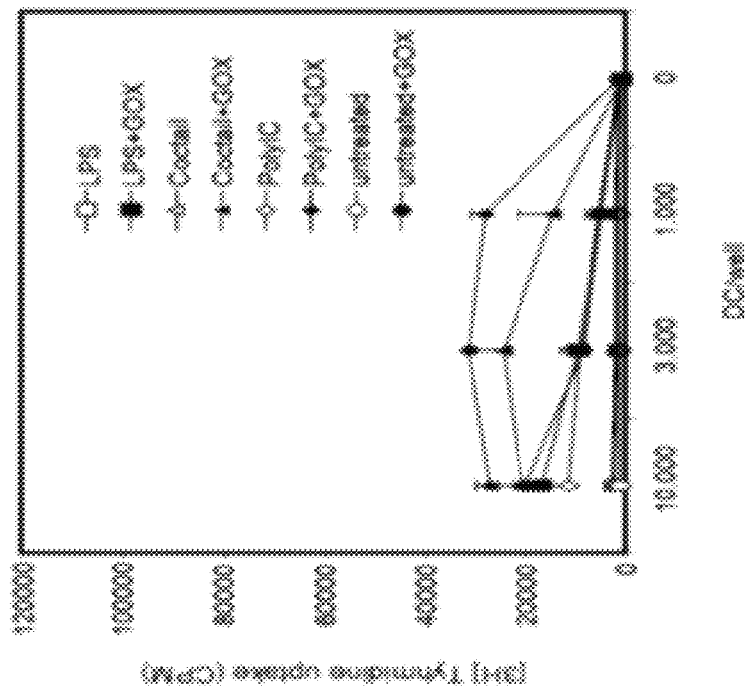
Figure 6A:
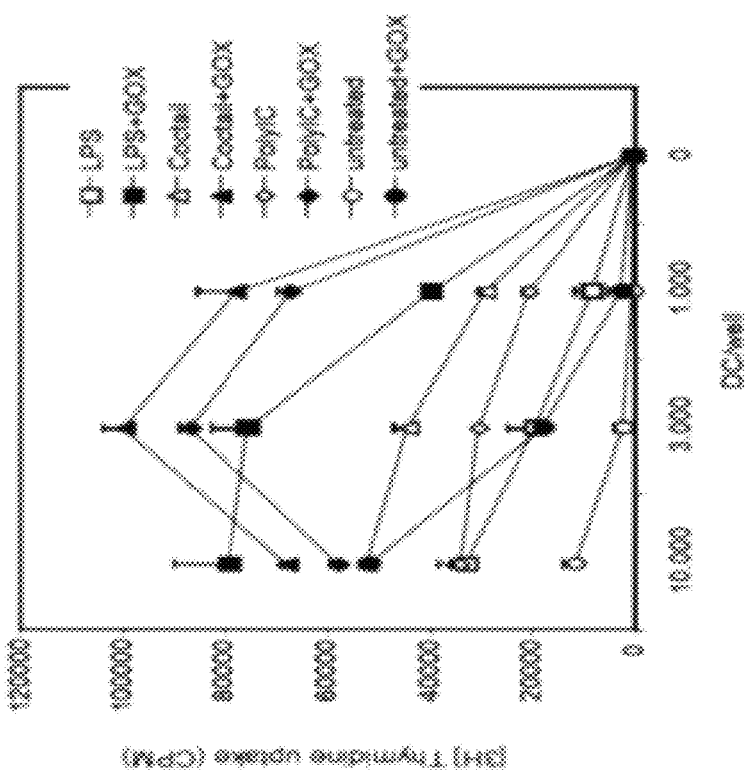

FIGS. 6A-6B show experimental data comparing the allogeneic and syngeneic T cell priming capability of immature and mature human DCs in vitro upon GOX treatment.

Human DCs were generated from monocytes and treated with different maturation stimuli overnight. Then the DCs were treated with GOX, washed and added to allogeneic (6A) or syngeneic (6B) T cell cultures. After 3 days the cultures were pulsed with [$^3$H]-thymidine to measure T cell proliferation. CPM=counts per minute. The data are representative for four and three independent experiments with similar results, respectively.

Thus, GOX treatment increases preferentially the allogeneic T cell priming capability of immature and mature human DCs in vitro.

Figure 7:
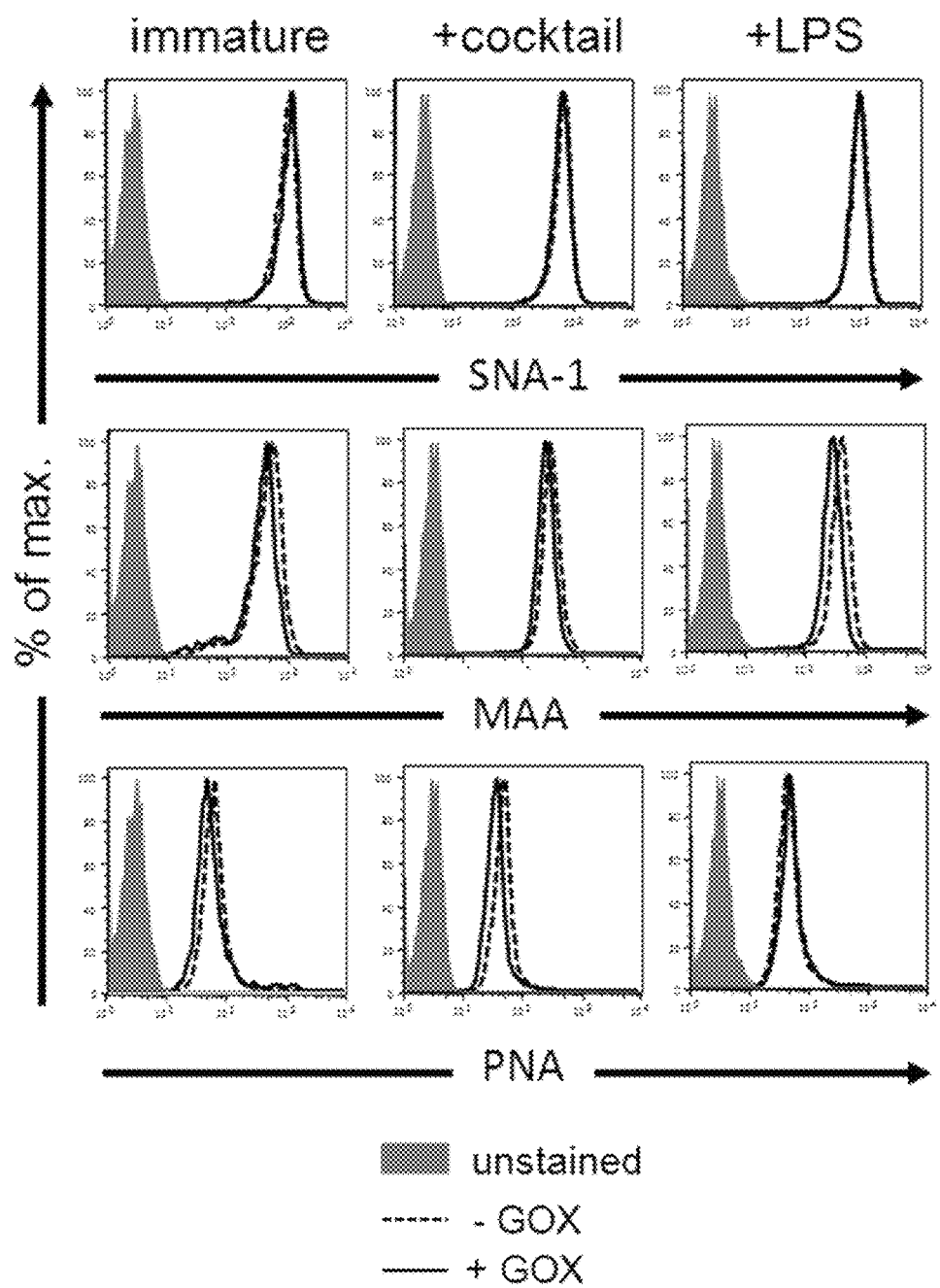

FIG. 7 shows experimental data addressing the question if GOX treatment of DCs alters surface lectin stainings.

The indicated lectin stainings on immature or LPS- or cocktail-matured DCs with or without additional GOX treatment were performed together with CD83 staining. Histograms for immature DCs were gated as CD83$^-$ and for mature DCs as CD83$^+$ cells. Data are representative of three independent experiments with similar results.

As can be seen from the data, GOX treatment of DCs does not alter surface lectin stainings.

Figure 8:
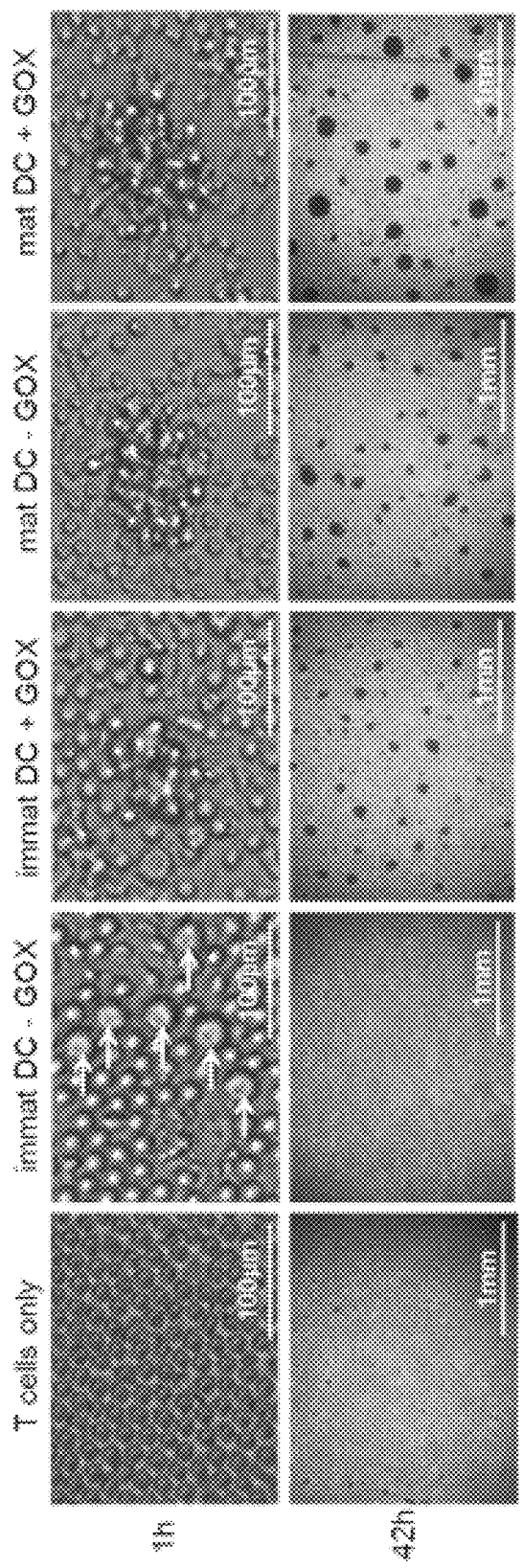

FIG. 8 shows experimental data addressing the question if GOX treatment of human DCs induces clustering with allogeneic T cells. Immature or mature DCs treated or not with GOX were co-cultured with allogeneic T cells for 1 h or 42 h in 96-well flat bottom plates before photographs were taken under phase contrast conditions. n=2

As can be seen from the data, GOX treatment of human immature DCs induces strong and rapid clustering with allogeneic T cells unlike DCs without GOX. GOX treatment of mature DCs induces larger cluster formation as compared without GOX treatment.

Thus, cluster formation with T cells can be used as a marker to distinguish GOX-treated from untreated immature DCs and increased clustering do detect GOX treatment of mature DCs.

Figure 9:
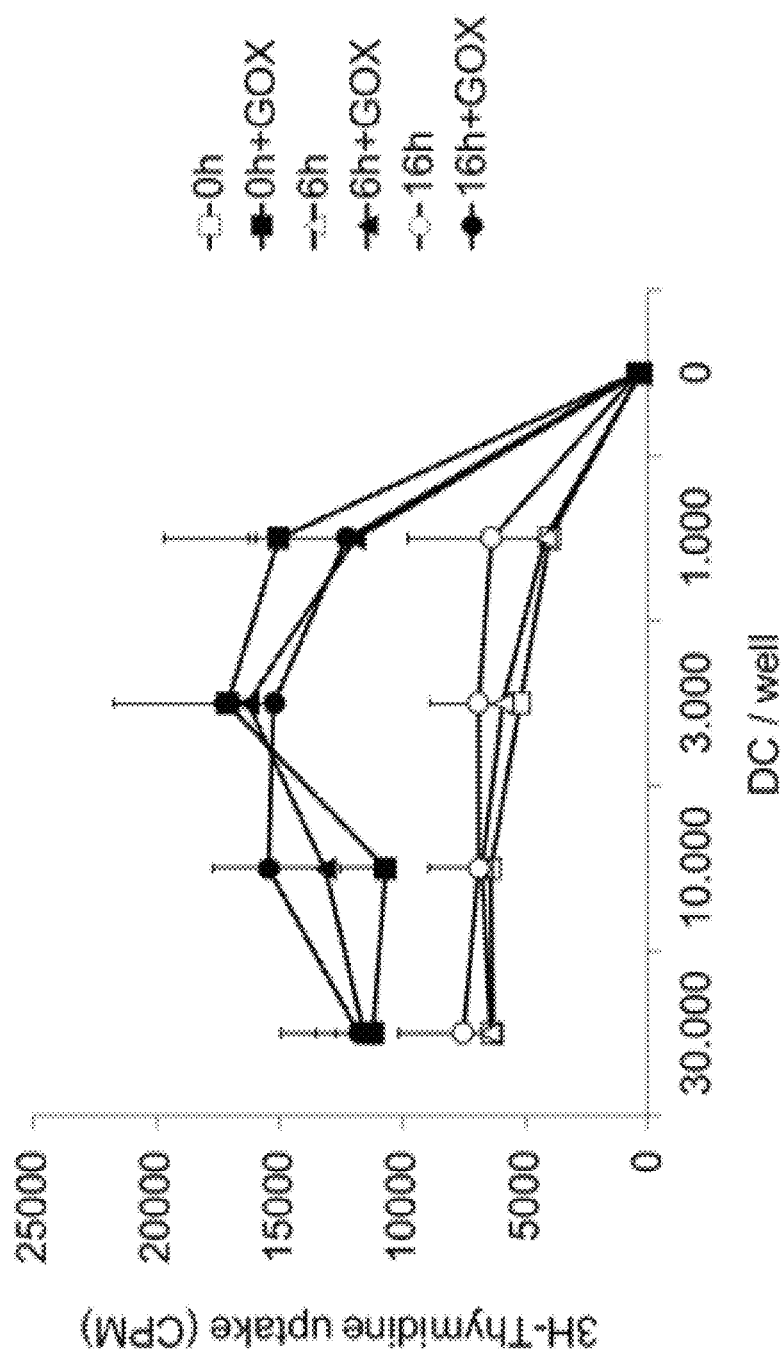

FIG. 9 shows experimental data to explore if the effects of GOX treatment of human DCs are stable. Human DCs were generated from monocytes and treated with different maturation stimuli overnight. Then the DCs were treated with GOX, washed and cultured for 0 h or 6 h at RT or 16 h at 37° C. before added to allogeneic T cells. After 3 days the cultures were pulsed with [$^3$H]-thymidine to measure T cell proliferation. CPM=counts per minute. The graphs represent pooled cpm values from three independent experiments with each performed in triplicates.

As can be seen from the data, GOX treatment of human DCs remain stable for 6 and 16 hours. Thus, the T cell stimulatory effects by GOX treatment as part of a clinical DC preparation procedure is retained, even when the cells may have to be transported for some hours from the cell culture laboratory to the patient until injection.

Figure 10:
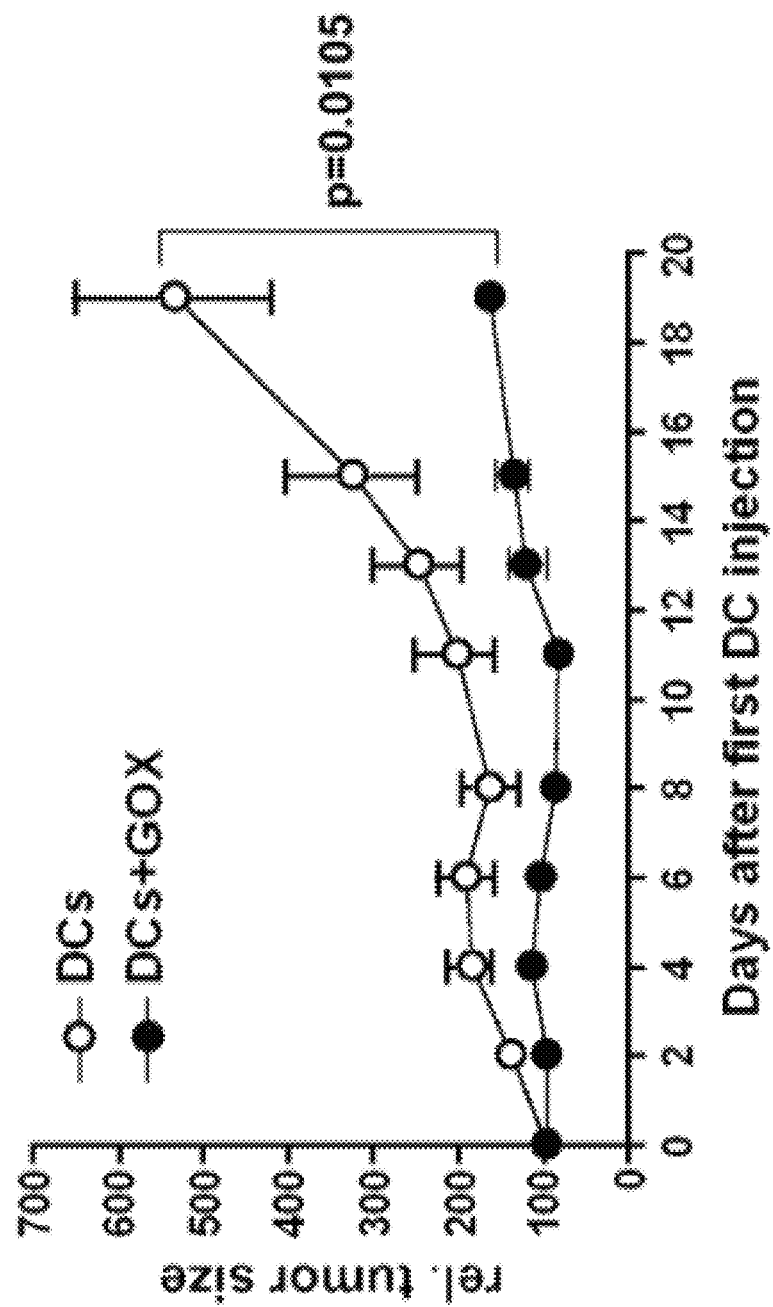

FIG. 10 shows experimental data to investigate if GOX-treatment of mature DCs further improves the effects of therapeutic vaccination with such DCs in a mouse tumor model. As can be seen from the data, GOX treatment of mature peptide-loaded DCs further improves their potential as anti-tumor vaccines.

In the following, reference is made to the examples, which are given to illustrate, not to limit the present invention.

EXAMPLES

Example 1

Generation and Maturation of Dendritic Cells

Murine DC Generation and Maturation

BM-DCs were generated as described in detail before (9). At d8 (day 8) cells were matured by addition of LPS (0.1-1 µg/ml, SIGMA), TNF (500 U/ml, Peprotech) or anti-CD40 (5 µg/ml, Biolegend) to the cultures for 16 h or as otherwise indicated.

Human DC Generation and Maturation

DC generation from human PBMCs (peripheral blood mononuclear cells) was adapted from (10) and was principally performed under conditions that fulfill GMP (good manufacturing practice) requirements as used for injection of DCs in patients. Peripheral blood was obtained from Blood Bank of the University of Würzburg and depleted of thrombocytes and plasma by using the Trima Accel® apheresis system (CaridianBCT, #80300) from healthy blood donors with consent of the Ethical Committee of the University of Würzburg. PBMCs were isolated by centrifugation in Lymphocyte Separation Medium LSM 1077 (PAA Laboratories GmbH, Cölbe) and plated in sterile Tissue culture dishes 100 mm (Greiner No 664160) at a density of $50\times10^6$ cells per dish in 10 ml culture medium RPMI 1640 without L-Glutamine (PAA Laboratories GmbH, Cölbe) with 1% heat-inactivated (30 min., 56° C.) human Serum, of the clot, Type AB (PAA Laboratories GmbH, Cölbe), 2 mM L-Glutamin (PAA 200 mM), Penicillin/Streptomycin (PAA 100×) and incubated at 37° C., 5% $CO_2$ for 1 h. After 1 h the non-adherent fraction (NAF) was removed and deep-frozen at −80° C. for later use as T cell source for the allogeneic mixed lymphocyte reaction (MLR). The dishes were washed twice with PBS without $Ca^{2+}$ or $Mg^{2+}$. Afterwards 10 ml of fresh, warm culture medium was added on the dish with the adherent monocytes and incubated for 16 h at 37° C., 5% $CO_2$. At day one the culture medium was taken off carefully so that loosely adherent cells were not removed and new culture medium containing 800 U/ml GM-CSF (Granulocyte macrophage colony-stimulating factor; Leukine® Sargramostim Bayer) and 250 U/ml IL-4 (Strathmann Biotec AG Hamburg) was added. Cytokines were added again at day 3 in 3 ml fresh medium (containing GM-CSF 800 U/ml and IL-4 25-250 U/ml) per dish and cultured until day 5. Maturation of human DCs was performed at $5\times10^5$ cells/well in 24 well plates with a maturation cocktail consisting of $PGE_2$ (1 μg/ml, SIGMA), TNF (1 ng/ml), IL-6 (1000 U/ml), and IL-1β (2 ng/ml, all Strathmann Biotec, Hamburg) as described (11). Alternatively, 0.1 μg/ml LPS (*E. coli*, 0127:B8, SIGMA) or 50 μg/ml Poly I:C (InvivoGen, Toulouse) were used.

GOX Treatment

Murine and human DCs were treated with GOX (2 U/ml, SIGMA, from *Dactylium dendroides*) for 90 min at 37° C. and washed with PBS always before adding maturation stimuli. For in vitro and in vivo priming with DCs GOX treatment was performed for 90 min (2 U/ml) after maturation of the DCs just before the injection.

FACS Analyses

For the staining $0.5\text{-}5\times10^5$ cells were incubated with the antibodies and respective isotype controls with buffer (PBS with 0.1% BSA, 0.2% sodium azide, 2 mM EDTA at 4° C. for 30 min. Then cells were washed and analyzed with an LSR II flow cytometer (BD) and FlowJo Cytometry Analysis Software (Tree Star Inc. Olten).

Antibodies to stain mouse cells were used at 1:300 dilution for MHC II (M5-114, PE, BD Pharmingen and Biolegend), and 1:100 dilution for CD80/FITC, CD86/FITC, 4-1BBL/PE and PD-L1/PE (Biolegend and eBioscience). Secondary staining was performed with streptavidin-PE conjugates (1:200, BD Pharmingen). Antibodies for human FACS analyses were HLA-DR/PE (1:50, BD Biosciences), CD83/APC (1:50, BD Biosciences), CD86/PE (1:25, BD Biosciences) and CD25/PE (1:50, Miltenyi Biotec).

The lectins PNA (peanut agglutinin, from *Arachis hypogaea*, recognizing β1-3-linked galactose/N-acetylgalactosamine), SNA-1 (*Sambucus nigra* lectin type-1, recognizing α2-6-linked sialic acid/galactose) and MAA (*Maackia amurensis* lectin, recognizing α2-3-linked sialic acid/galactose) were used for detection of sugar linkages of the glycocalix on the DC surface as FITC-conjugates (EY laboratories).

ELISA

Murine and human cytokine detection were performed with commercial kits according to the manufacturer's instructions from the following sources: mouse IL-6 (BD Biosciences), mouse IL-12p40 (BD Biosciences), human IL-6 (R&D Systems), human IL-12p40 (BD Biosciences).

Allogeneic MLR (Mixed Lymphocyte Reaction)

Mouse: DCs were cultured as described until d8, treated for 90 min with GOX, then transferred into a 24 well plate at $5\times10^5$ cells/well and stimulated overnight for 16 h with maturation reagents. After washing titrated numbers of DCs were added to $2\times10^5$ total lymph node cells as a source of T cells in a 96-well flat bottom plate (FALCON).

Human: At day 5 of DC culture after PBMC (peripheral blood mononuclear cells) preparation NAF from other blood donors (allogeneic) were prepared for allogeneic MLR and cultured over night. At day 6 the stimulated DC were harvested and seeded into two 96-well flat-bottom plates as triplicates at titrated amounts of DCs as indicated. Then $2\times10^5$ NAF from different donor were added.

Both human and mouse: After 3 days cultures were pulsed with 1 μCi/well [$^3$H]-Thymidin (Hartmann Analytic, Braunschweig) for 16 h and then harvested onto glass fiber filter mats (PerkinElmer, USA), scintillation wax added and counted in a 1450 Microbeta Counter (Tomtec) to measure cell proliferation.

In Vivo Priming of Mice with KLH

BM-DCs from C57BL/6 mice were treated at d8 with KLH (50 μg/ml, high purity, endotoxin-free, sterile, Calbiochem®/Merck Millipore #374825) and with or without LPS overnight. Then cells were treated directly with GOX as mentioned above, washed and injected with $4\times10^5$ cells/mouse s.c. into the footpads of syngeneic mice. After 11 days the popliteal and inguinal lymph nodes and spleens were removed. Spleens were treated for erythrocyte lysis with 1.66% $NH_4Cl$ in PBS for 3 min at 37° C. Single cell suspensions from both types of organs were restimulated with KLH at titrated doses in serum-free HL-1 medium (Bio Whittaker®/Lonza) for three days before cultures were pulsed with 1 μCi/well [$^3$H]-Thymidin (Hartmann Analytic, Braunschweig) for 16 h and then harvested onto glass fiber filter mats (PerkinElmer, USA), scintillation wax added and counted in a 1450 Microbeta Counter (Tomtec) to measure cell proliferation.

Therapeutic Vaccination with (GOX-Treated) DCs in Mice

MO4-10 tumor cells (kindly provided by Natalio Garbi, Bonn), which represent a subclone of B16-ova originally generated by Kenneth L. Rock (15), were injected at $1\times10^6$ cells/mouse s.c. into the flanks of C57BL/6-albino mice (each group n=5 mice). Seven days later $1\times10^7$ OT-I and $1\times10^7$ OT-II pooled lymph node and spleen cells were injected i.v. into each mouse.

BM-DC were generated from C57BL/6 mice as described in detail before (9). DCs were harvested at days 6, 8 and 10, at each time point stimulated with LPS (0.1 µg/ml SIGMA) plus anti-CD40 (5 µg/ml, clone 1C10, Biolegend) plus $OVA_{323-339}$ peptide (10 µM) plus $OVA_{257-264}$ peptide (10 µM) for 4 h at 37° C. and 5% $CO_2$ as described before (13, 14). Parallel DC cultures remained untreated or received the additionally treatment with GOX (2 U/ml) for the last 90 min of the above-mentioned stimulation. After washing the two types of DCs were counted and injected at $2\times10^6$ DCs/200 µl s.c. into the contra-lateral flank. Thus, each mouse received three DC injections at 1, 3 and 5 days after the T cell transfer. Tumor growth was followed by caliper measurement every second day after the first DC injection.

Example 2

Murine BM-DCs do not Show Changes in Maturation Markers or Cytokine Production after GOX Treatment All methods mentioned in this example were carried out as described in Example 1.

BM-DCs were generated and treated with various maturation stimuli alone or in combination with GOX. GOX treatment was performed on untreated DCs or after the overnight maturation of DCs. Analysis of surface MHC II and CD86 expression showed activity of the maturation stimuli as expected, but no further up-regulation by GOX (FIG. 1A). Additional analyses on other co-stimulatory or co-inhibitory markers such as CD80, 4-1BBL or PD-L1 on immature DCs revealed no effects (FIG. 1B).

Since secretion of pro-inflammatory cytokines by DCs is another critical component not only for DC maturation but also T helper cell polarization, the levels of IL-6 and IL-12 secreted by BM-DCs after various stimulations alone or in combination with GOX was tested. Also here, no effects of GOX on the DCs could be observed (FIG. 2). Together, mouse BM-DCs seem unresponsive to GOX treatment with respect to various maturation criteria.

Example 3

GOX Treatment of Murine DCs Increases T Cell Priming Capability In Vitro and In Vivo All methods mentioned in this example were carried out as described in Example 1.

To test whether GOX-treated DCs are functionally modified by treatment with GOX, in vitro and in vivo T cell priming assays were carried out.

Immature and mature BM-DCs were treated or not with GOX and then titrated into cultures containing allogeneic T cells. After 3 days T cell proliferation was measured. Interestingly, both immature and mature DCs improved their T cell stimulatory potential in vitro (FIG. 3A). For therapeutical application of DCs, their in vivo priming potential for exogenously pulsed antigens and their successful migration into the T cell areas of lymphoid organs are more relevant. Thus, BM-DCs were loaded with KLH antigen that is also used in clinical studies as a bystander antigen supporting tumor peptide vaccinations with DCs (12). The DCs were matured with LPS or not for the period of the 4 h simultaneously during KLH pulse before the 90 min GOX treatment and subcutaneous injection into syngeneic mice. After 11 days the draining lymph nodes and the spleens were removed and single cell suspensions restimulated with KLH. Immature DC were largely unable to prime the mice, while LPS-DCs showed a clear response in the lymph nodes but little in the spleen (FIG. 3B). In contrast, both immature and mature DCs that were additionally treated with GOX showed an increased priming potential, also by immature DCs and in the spleen, indicating that GOX-aided DC vaccination provokes not only a stronger but also more systemic T cell response against an antigen.

Example 4

Human Monocyte-Derived DCs Mature Upon GOX Treatment

All methods mentioned in this example were carried out as described in Example 1.

To test also human DCs for their response to GOX, the murine experiments (Examples 2 and 3) were repeated with human immature and mature DCs. Surprisingly, while murine DC surface markers remained unaffected after GOX treatment, human immature DCs responded on GOX by upregulating HLA-DR, CD83, CD86 and CD25 (FIGS. 4A, 4B). Combined GOX treatment with different typical maturation stimuli such as by cytokine cocktail, Poly I:C or LPS could only weakly further improve the maturation state that was reached with GOX alone, when the cells from the same donor were compared (FIG. 4C).

When testing the supernatants of these cultures, it was found that GOX alone could not induce IL-12p40, but stimulated IL-6 release (FIG. 5A). Combination of GOX with the other maturation stimuli dramatically further augmented IL-6 release, but did only marginally improve IL-12p40 production when cells from the same donor were compared (FIG. 5B).

Together, GOX treatment of human DCs induces strong maturation as detected by surface markers and IL-6 release, but does not substantially provoke IL-12p40 production. Combination with typical maturation stimuli had mild effects on further surface marker and IL-12p40 up-regulation, but enhanced IL-6 release between 163- and 2763-fold.

Example 5

Human GOX-Treated DCs Show Increased T Cell Priming Potential In Vitro

To test how the GOX-mediated maturation translates into T cell priming, the differentially treated DCs were cultured with allogeneic or syngeneic naive T cells and their proliferation after 3 days in culture was measured. GOX treatment of immature DCs clearly enabled T cell priming but combination of GOX with any maturation stimulus enhanced T cell proliferation (FIG. 6A, B). In fact 1000 DCs after GOX plus maturation stimulus treatment were as or even more effective than 10000 DCs treated with maturation stimuli alone, indicating an at least 10-fold improved T cell priming capability. Also the proliferation of syngeneic T cells could be induced (FIG. 6B), but did not exceed the levels of allogeneic T cell proliferation stimulated by immature DCs (FIG. 6A). Thus, a preferential expansion of allogeneic over syngeneic T cells could be achieved by GOX treatment of DCs.

Example 6

GOX Treatment of DCs does not Modify Glycocalix Structure

All methods mentioned in this example were carried out as described in Example 1.

In this experiment, it was tested whether GOX treatment of DCs would modify galactose moieties of the glycocalix in such a way that the binding of FITC-conjugated plant lectins to the DC surface would be modified. Lectins were selected that can detect distal disaccharide linkage structures of galactose with other sugars. The results indicate that neither binding of PNA (β1-3-linked galactose/N-acetylgalactosamine), SNA-1 (α2-6-linked sialic acid/galactose) nor MAA (α2-3-linked sialic acid/galactose) was altered by GOX treatment (FIG. 7). These data suggest that the three-dimensional structure of the glycocalix is not modified by GOX.

Example 7

Rapid and Strong Clustering with Allogeneic T Cells Marks GOX-Treated DCs

All methods mentioned in this example were carried out as described in Example 1.

Increased T cell stimulation may result from more intense interactions between DCs and T cells that can be visualized as cluster formations. Cultures prepared as for the mixed lymphocyte reactions were photographed after 1 h or 42 h. The data show the absence of clusters when T cells were cultured alone or with immature DC that were not treated with GOX (FIG. 8). However, immature DC treated with GOX rapidly clustered with T cells already after 1 h, thereby marking them for a preceding GOX treatment. As expected cluster formation appeared with mature DCs and GOX treatment further increased with GOX treatment (FIG. 8). Thus, GOX treatment of immature and mature DCs promotes more intense interactions during antigen presentation as indicated by cluster formation.

Example 8

The Increased T Cell Stimulatory Effect of DCs by GOX-Treatment Remains Stable

All methods mentioned in this example were carried out as described in Example 1.

The enzymatic modification of the DC surface by GOX may be transient and reversible after removal of GOX by the turnover of cell surface molecules and metabolic activity. Therefore it was tested whether the increased T cell stimulation of GOX-treated mature DCs remained stable after maturation and GOX treatment for 6 h at RT or 16 h at 37° C. before adding to allogeneic T cells (FIG. 9). The data reveal that no loss of T cell stimulatory capacity occurs under these conditions, allowing the GOX treatment of DCs also under clinical conditions during a transfer of GOX-DCs from the cell culture facility to the patient in the clinic.

Example 9

GOX-Treatment of LPS-Plus Anti-CD40-Matured DCs Improves their Anti-Tumor Vaccination Capacity in Mice All methods mentioned in this example were carried out as described in Example 1.

In this experiment, it was tested whether GOX-treatment of mature DCs would further improve the therapeutic vaccination success of DCs in a pre-clinical tumor model of therapeutic vaccination with mice that carried an established tumor. To show this, OVA$^+$B16 melanoma cells (subclone MO4-10) were subcutaneously injected into the flanks of mice. One week later OVA-specific CD4$^+$ (OT-II) and CD8$^+$ (OT-I) T cells were adoptively transferred i.v. and one day later the therapeutic DC vaccinations started. DCs were loaded with the MHC I- and MHC II-restricted OVA peptides plus LPS and anti-CD40 antibodies for 4 h before s.c. injection into the contralateral flank. One experimental group of DCs received additional GOX treatment. The combination of maturation reagents LPS plus anti-CD40 was chosen due to its rather high immunogenicity (13, 14). Here it was tested whether GOX-treatment of these mature DCs would further improve their therapeutic potential. Injection of LPS/CD40-matured DC delayed tumor growth between days 4 and 8, while the same DCs additionally treated with GOX fully controlled further tumor growth over a period of 2 weeks. These results indicate that GOX treatment of mature peptide-loaded DCs further improve their potential as anti-tumor vaccines.

The results of all 9 time points were analyzed together by a paired, two-tailed Students's t test. The result was significant as p=0.0105.

The features of the present invention disclosed in the specification, the claims, and/or in the accompanying drawings may, both separately and in any combination thereof, be material for realizing the invention in various forms thereof.

REFERENCES

1. Berger, T. G., H. Schulze-Koops, M. Schafer, E. Muller, and M. B. Lutz. 2009. Immature and maturation-resistant human dendritic cells generated from bone marrow require two stimulations to induce T cell anergy in vitro. *PLoS One* 4: e6645.
2. Lutz, M. B. 2004. IL-3 in dendritic cell development and function. A comparison with GM-CSF and IL-4. *Immunobiology* 209: 79-87.
3. Naik, S. H. 2008. Demystifying the development of dendritic cell subtypes, a little. *Immunol Cell Biol* 86: 439-452.
4. Lutz, M. B., and G. Schuler. 2002. Immature, semi-mature and fully mature dendritic cells: which signals induce tolerance or immunity? *Trends Immunol* 23: 445-449.
5. Buonaguro, L., A. Petrizzo, M. L. Tornesello, and F. M. Buonaguro. 2011. Translating tumor antigens into cancer vaccines. *Clin Vaccine Immunol* 18: 23-34.
6. Tacken, P. J., I. J. de Vries, R. Torensma, and C. G. Figdor. 2007. Dendritic-cell immunotherapy: from ex vivo loading to in vivo targeting. *Nature reviews* 7: 790-802.
7. Reis e Sousa, C. 2006. Dendritic cells in a mature age. *Nature reviews* 6: 476-483.
8. Palucka, A. K., H. Ueno, J. W. Fay, and J. Banchereau. 2007. Taming cancer by inducing immunity via dendritic cells. *Immunol Rev* 220: 129-150.
9. Lutz, M. B., N. Kukutsch, A. L. Ogilvie, S. Rossner, F. Koch, N. Romani, and G. Schuler. 1999. An advanced culture method for generating large quantities of highly pure dendritic cells from mouse bone marrow. *J Immunol Methods* 223: 77-92.
10. Romani, N., D. Reider, M. Heuer, S. Ebner, E. Kampgen, B. Eibl, D. Niederwieser, and G. Schuler. 1996. Generation of mature dendritic cells from human blood. An improved method with special regard to clinical applicability. *J Immunol Methods* 196: 137-151.
11. Jonuleit, H., U. Kuhn, G. Muller, K. Steinbrink, L. Paragnik, E. Schmitt, J. Knop, and A. H. Enk. 1997. Pro-inflammatory cytokines and prostaglandins induce maturation of potent immunostimulatory dendritic cells under fetal calf serum-free conditions. *European journal of immunology* 27: 3135-3142.

12. Schuler-Thurner, B., E. S. Schultz, T. G. Berger, G. Weinlich, S. Ebner, P. Woerl, A. Bender, B. Feuerstein, P. O. Fritsch, N. Romani, and G. Schuler. 2002. Rapid induction of tumor-specific type 1 T helper cells in metastatic melanoma patients by vaccination with mature, cryopreserved, peptide-loaded monocyte-derived dendritic cells. *The Journal of experimental medicine* 195: 1279-1288.
13. Menges, M., S. Rössner, C. Voigtländer, H. Schindler, N. A. Kukutsch, C. Bogdan, K. Erb, G. Schuler, and M. B. Lutz. 2002. Repetitive injections of dendritic cells matured with tumor necrosis factor alpha induce antigen-specific protection of mice from autoimmunity. *The Journal of experimental medicine* 195: 15-21.
14. Hänig, J., and M. B. Lutz. 2008. Suppression of mature dendritic cell function by regulatory T cells in vivo is abrogated by CD40 licensing. *J. Immunol.* 180: 1405-1413.
15. Falo, L. D., Jr., M. Kovacsovics-Bankowski, K. Thompson, and K. L. Rock. 1995. Targeting antigen into the phagocytic pathway in vivo induces protective tumour immunity. *Nature medicine* 1: 649-653.

The invention claimed is:

1. A method for producing dendritic cells with increased capability to activate T cells, wherein said method comprises obtaining dendritic cells from bone marrow, or from monocytes or other hematopoietic dendritic cell precursor or progenitor cells by in vitro differentiation, and treating said dendritic cells with galactose oxidase in vitro, wherein said dendritic cells are human cells.

2. The method according to claim 1, wherein said dendritic cells to be treated with galactose oxidase are mature dendritic cells.

3. The method according to claim 1, wherein said dendritic cells are not treated with any maturation stimulus before, during or after said treatment with galactose oxidase.

4. The method according to claim 1, wherein said dendritic cells are not treated with neuraminidase before, during or after said treatment with galactose oxidase.

5. The method according to claim 1, wherein said dendritic cells with increased capability to activate T cells present at least one tumor antigen.

6. The method according to claim 1, wherein said galactose oxidase treatment is for 1-5 hours at a concentration of 0.1-20 U/ml.

7. The method according to claim 1, wherein said galactose oxidase treatment is for 1-2 hours at a concentration of 1-5 U/ml.

* * * * *